United States Patent
Kawai et al.

(10) Patent No.: US 11,536,677 B2
(45) Date of Patent: *Dec. 27, 2022

(54) GAS DETECTION DEVICE, GAS SENSOR SYSTEM, FUEL CELL VEHICLE, AND HYDROGEN DETECTION METHOD

(71) Applicant: Panasonic Intellectual Property Management Co., Ltd., Osaka (JP)

(72) Inventors: Ken Kawai, Osaka (JP); Koji Katayama, Nara (JP); Shinichi Yoneda, Kyoto (JP)

(73) Assignee: NUVOTON TECHNOLOGY CORPORATION JAPAN, Kyoto (JP)

( * ) Notice: Subject to any disclaimer, the term of this patent is extended or adjusted under 35 U.S.C. 154(b) by 811 days.

This patent is subject to a terminal disclaimer.

(21) Appl. No.: 16/471,864

(22) PCT Filed: Dec. 18, 2017

(86) PCT No.: PCT/JP2017/045247
§ 371 (c)(1),
(2) Date: Jun. 20, 2019

(87) PCT Pub. No.: WO2018/123674
PCT Pub. Date: Jul. 5, 2018

(65) Prior Publication Data
US 2020/0096465 A1    Mar. 26, 2020

(30) Foreign Application Priority Data
Dec. 28, 2016  (JP) .............................. JP2016-256892

(51) Int. Cl.
*G01N 27/12*   (2006.01)
*B60L 50/71*   (2019.01)
(Continued)

(52) U.S. Cl.
CPC ............. *G01N 27/122* (2013.01); *B60K 1/04* (2013.01); *B60L 50/71* (2019.02); *G01N 27/12* (2013.01);
(Continued)

(58) Field of Classification Search
CPC .... G01N 27/041; G01N 27/045; G01N 27/12; G01N 27/122; G01N 27/125;
(Continued)

(56) References Cited

U.S. PATENT DOCUMENTS

2013/0250658 A1   9/2013  Wei et al.
2013/0311108 A1*  11/2013 Stetter .................. G01N 27/128
                                                        702/22

(Continued)

FOREIGN PATENT DOCUMENTS

CN    107315034 A    11/2017
GB    2182448 B      1/1989
(Continued)

OTHER PUBLICATIONS

Chinese Office Action and Search Report dated May 19, 2021 issued in corresponding Chinese Patent Application No. 201780080428.3; with partial English translation.
(Continued)

*Primary Examiner* — Benjamin R Schmitt
(74) *Attorney, Agent, or Firm* — McDermott Will & Emery LLP

(57) ABSTRACT

A gas detection device includes a gas sensor and a drive circuit. The drive circuit includes a measurement circuit, a power supply circuit, and a control circuit. The gas sensor includes a first electrode, a second electrode, a metal-oxide layer disposed between the first electrode and the second electrode, and an insulating film that covers the first electrode, the second electrode, and the metal-oxide layer, and
(Continued)

has an opening that exposes part of a main surface of the second electrode. A resistance value of the metal-oxide layer decreases when gas containing hydrogen atoms contact the second electrode. When the resistance value of the metal-oxide layer falls outside a predetermined range, the drive circuit applies a predetermined voltage between the first electrode and the second electrode to restore the resistance value of the metal-oxide layer back into the predetermined range.

16 Claims, 12 Drawing Sheets

(51) Int. Cl.
*G01N 33/00* (2006.01)
*H01L 45/00* (2006.01)
*H01M 8/04082* (2016.01)
*H01M 8/0438* (2016.01)
*B60K 1/04* (2019.01)
*B60K 15/03* (2006.01)
*G07C 5/00* (2006.01)

(52) U.S. Cl.
CPC ......... *G01N 27/125* (2013.01); *G01N 33/005* (2013.01); *H01L 45/08* (2013.01); *H01L 45/1233* (2013.01); *H01L 45/1253* (2013.01); *H01L 45/146* (2013.01); *H01M 8/04201* (2013.01); *H01M 8/04425* (2013.01); *B60K 15/03* (2013.01); *B60K 2015/0321* (2013.01); *B60K 2015/03315* (2013.01); *G07C 5/008* (2013.01); *H01M 2250/20* (2013.01)

(58) Field of Classification Search
CPC ............. G01N 27/128; G01N 27/4163; G01N 33/0006; G01N 33/005; G01N 33/007
See application file for complete search history.

(56) References Cited

U.S. PATENT DOCUMENTS

2017/0131227 A1* 5/2017 Homma ............. H01M 8/0444
2017/0307557 A1 10/2017 Muraoka et al.

FOREIGN PATENT DOCUMENTS

| JP | S59-58348 A | 4/1984 |
|---|---|---|
| JP | S61-191954 A | 8/1986 |
| JP | H11-66464 A | 3/1999 |
| JP | 2003-240746 A | 8/2003 |
| WO | 2013/051267 A1 | 4/2013 |

OTHER PUBLICATIONS

International Search Report (ISR) dated Mar. 6, 2018 in International (PCT) Application No. PCT/JP2017/045247.
J. Yu et al., "Hydrogen gas sensing properties of Pt/Ta2O5 Schottky diodes based on Si and SiC substrates", Sensors and Actuators A: Physical, 172 (2011), pp. 9-14.

* cited by examiner

GAS DETECTION DEVICE, GAS SENSOR SYSTEM, FUEL CELL VEHICLE, AND HYDROGEN DETECTION METHOD

CROSS-REFERENCE OF RELATED APPLICATIONS

This application is the U.S. National Phase under 35 U.S.C. § 371 of International Patent Application No. PCT/JP2017/045247, filed on Dec. 18, 2017, which in turn claims the benefit of Japanese Application No. 2016-256892, filed on Dec. 28, 2016, the entire disclosures of which Applications are incorporated by reference herein.

TECHNICAL FIELD

The present disclosure relates to a gas detection device including a gas sensor, a gas sensor system, a fuel cell vehicle, and a hydrogen detection method.

BACKGROUND ART

PTL 1 discloses a gas sensor that detects, as a change in a resistance value, a presence of hydrogen gas. The gas sensor includes a material made by adding palladium (Pd) and glass to tantalum pentoxide ($Ta_2O_5$), and platinum (Pt) electrodes sandwiching this material.

Non-Patent Literature (NPL) 1 discloses $Pt/Ta_2O_5$ Shottky diodes for hydrogen sensing. In the Shottky diodes, hydrogen molecules are dissociated into hydrogen atoms on the surface of catalyst Pt.

PTL 2 discloses a gas leak alarm which includes a lifespan determiner that determines the lifespan of a gas sensor, and a switching circuit that sequentially switches from one sensor element to another in accordance with a result of the determination.

CITATION LIST

Patent Literature

PTL 1: Japanese Unexamined Patent Application Publication No. 59-58348
PTL 2: Japanese Unexamined Patent Application Publication No. 11-66464

Non-Patent Literature

NPL 1: J. Yu et al. "Hydrogen gas sensing properties of $Pt/Ta_2O_5$ Shottky Diodes based on Si and SiC substrates". Sensors and Actuators A 172 (2011) 9-14

SUMMARY OF THE INVENTION

Technical Problem

The present disclosure provides a gas detection device that is highly capable of saving power and detecting hydrogen-containing gas with good sensitivity, and has a simple structure and a long device lifespan.

Solutions to Problem

A gas detection device according to one aspect of the present disclosure includes: a gas sensor; and a drive circuit that applies a predetermined voltage to the gas sensor. The gas sensor includes: a first electrode; a second electrode; a metal-oxide layer that is disposed between the first electrode and the second electrode, and includes a bulk region and a local region surrounded by the bulk region, the local region having a degree of oxygen deficiency higher than a degree of oxygen deficiency of the bulk region; and an insulating film that covers the first electrode, the second electrode, and the metal-oxide layer, and has an opening that exposes part of a main surface of the second electrode. A resistance value of the metal-oxide layer decreases when the gas contacts the second electrode, the gas containing hydrogen atoms. When the resistance value of the metal-oxide layer falls outside a predetermined range that is set within a range of resistance values of the metal-oxide layer before the gas contacts the second electrode, the drive circuit applies the predetermined voltage between the first electrode and the second electrode to restore the resistance value back into the predetermined range.

Advantageous Effect of Invention

A gas detection device according to one aspect of the present disclosure is highly capable of saving power and detecting hydrogen-containing gas with good sensitivity, and has a simple structure and a long device lifespan.

DESCRIPTION OF EXEMPLARY EMBODIMENTS

Figure 1A:
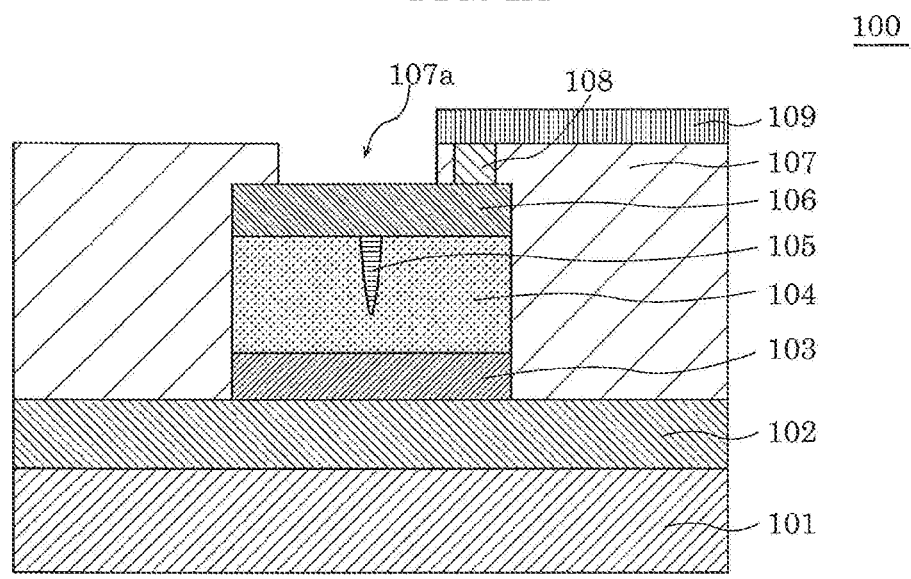
FIG. 1A is a cross-sectional view illustrating an example of a gas sensor according to Embodiment 1.

Underlying Knowledge Forming Basis of the Present Disclosure

The inventors of the present disclosure have found the following problems in a conventional gas sensor, as a result of dedicating their works on the study of the conventional gas sensor.

With a conventional gas sensor, an element that detects gas is heated at 100 degrees Celsius or higher in order to enhance sensitivity in detecting hydrogen-containing gas. The power consumption of the conventional gas sensor is therefore approximately 100 mW at the lowest. Accordingly, when the conventional gas sensor is used in an on-state at all times, a problem is that the amount of power consumption increases.

In consideration of degradation and a lifespan of a sensor element, other conventional gas sensor uses a plurality of sensor elements, which are previously provided in a device, by sequentially switching from one sensor element to another each time the lifespan of one sensor element reaches its end. This requires, for example, a structure for retaining unused sensor elements without deteriorating them, and a problem is that it is difficult to make the lifespan of a device longer with a simple structure.

The gas detection device according to one aspect of the present disclosure is highly capable of saving power and detecting hydrogen-containing gas with good sensitivity, and has a simple structure and a long device lifespan.

Embodiments of the present disclosure will now be described with reference to the drawings.

In the drawings, like reference signs are assigned to elements presenting substantially identical structures, operations, and effects, and duplicate descriptions are omitted. The numerical values, materials, compositions, shapes, methods of forming films, the connection between elements, etc. described in the following are all mere examples for specifically illustrating the embodiments of the present disclosure, and the present disclosure is not limited to these examples. Among elements in the following embodiments, those not recited in any one of broadest, independent claims are described as optional elements.

Embodiment 1

Structure of Gas Sensor

A gas sensor according to Embodiment 1 is a gas sensor having a metal-insulator-metal (MIM) structure in which a resistive film (metal-oxide layer) and metal films are stacked. By utilizing both self-heating and gas sensitivity in a local region formed inside the resistive film, the gas sensor is capable of detecting hydrogen-containing gas without heating with a heater. Here, hydrogen-containing gas is a generic term for gas that is made up of molecules including hydrogen atoms, and may contain, for example, hydrogen, methane, alcohol, etc.

FIG. 1A is a cross-sectional view illustrating an example of a structure of gas sensor 100 according to Embodiment 1.

Figure 1B:
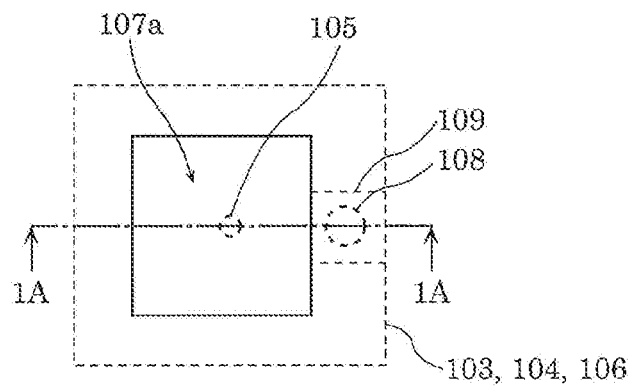
FIG. 1B is a top view illustrating the example of the gas sensor according to Embodiment 1.

FIG. 1B is a top view illustrating the example of the structure of gas sensor 100 according to Embodiment 1. A cross section shown in FIG. 1A corresponds to a cross section taken along the cutting line 1A-1A and viewed in a direction the arrows are pointing in FIG. 1B.

Gas sensor 100 includes substrate 101, insulating film 102 formed on substrate 101, first electrode 103 formed above insulating film 102, second electrode 106, resistive film 104 sandwiched between first electrode 103 and second electrode 106, insulating film 107, via 108, and wiring 109. First electrode 103 and second electrode 106 are disposed such that their main surfaces face each other, and resistive film 104 is disposed in contact with the main surfaces of first electrode 103 and second electrode 106.

Insulating film 107 is provided with opening 107a for allowing second electrode 106 to contact a target gas to be examined. Stated differently, insulating film 107 covers first electrode 103, second electrode 106, and resistive film 104 while at least part of a main surface (the other main surface opposite a main surface contacting resistive film 104) of second electrode 106 is uncovered by insulating film 107, and is thus exposed.

Resistive film 104 lies between first electrode 103 and second electrode 106. A resistance value of resistive film 104 reversibly changes based on an electric signal provided between first electrode 103 and second electrode 106. For example, a resistive state of resistive film 104 reversibly transitions between a high-resistance state and a low-resistance state according to a voltage (potential difference) applied between first electrode 103 and second electrode 106. The resistive state of resistive film 104 transitions, for example, from the high-resistance state to the low-resistance state in response to hydrogen-containing gas brought into contact with second electrode 106.

Resistive film 104 includes, inside, local region 105 that is disposed in contact with second electrode 106 and is not contacting first electrode 103. A degree of oxygen deficiency in local region 105 is higher than that in the surrounding region (i.e., a bulk region in resistive film 104). The degree of oxygen deficiency in local region 105 reversibly changes depending on the application of the electric signal between first electrode 103 and second electrode 106, and also on the presence or absence of hydrogen-containing gas in the gas that second electrode 106 contacts. Local region 105 is a minute region that includes a filament (conductive path) made up of oxygen defect sites.

Insulating film 107 is provided with via 108 penetrating through insulating film 107 and being connected to second electrode 106, in a portion covering the main surface of second electrode 106. Wiring 109 is disposed on via 108.

In the present disclosure, the "degree of oxygen deficiency" of a metal oxide is a ratio of the amount of oxygen deficient in the metal oxide to the amount of oxygen in an oxide having a stoichiometric composition consisting of the same elements as those of the metal oxide (here, the amount of oxygen deficient is a value obtained by subtracting the amount of oxygen in the metal oxide from the amount of oxygen in the metal oxide having the stoichiometric composition). If a plurality of metal oxides, each of which has a stoichiometric composition consisting of the same elements as those of the metal oxide, is present, the degree of oxygen deficiency of the metal oxide is defined based on one having the highest resistance value among the metal oxides having the stoichiometric composition. A metal oxide having the stoichiometric composition is more stable and has a higher resistance value compared to a metal oxide having a different composition.

For example, when a metal is tantalum (Ta), an oxide having the stoichiometric composition according to the above-described definition is $Ta_2O_5$, and can be expressed as $TaO_{2.5}$. The degree of oxygen deficiency of $TaO_{2.5}$ is 0%, and the degree of oxygen deficiency of $TaO_{1.5}$ results from (2.5−1.5)/2.5, i.e., 40%. In an oxygen-excess metal oxide, the degree of oxygen deficiency is a negative value. In the present disclosure, the degree of oxygen deficiency may be a positive value, zero, or a negative value, unless otherwise specified.

An oxide having a low degree of oxygen deficiency is more similar to an oxide having a stoichiometric composition and therefore has a high resistance value, whereas an oxide having a high degree of oxygen deficiency is more similar to a metal constituting an oxide and therefore has a low resistance value.

The term "oxygen content" is a rate of the number of oxygen atoms based on a total number of atoms. For example, the oxygen content of $Ta_2O_5$ is the rate of the number of oxygen atoms based on the total number of atoms, which is expressed by (O/(Ta+O)), i.e., 71.4 atm %. Accordingly, an oxygen-deficient tantalum oxide has an oxygen content higher than 0 atm % and lower than 71.4 atm %.

Local region 105 is formed in resistive film 104 by applying an initial break voltage between first electrode 103 and second electrode 106. In other words, the initial break voltage is a voltage applied between first electrode 103 and second electrode 106 for forming local region 105. An absolute value of the initial break voltage may be greater than that of a write-in voltage. The write-in voltage is a voltage applied between first electrode 103 and second electrode 106 for causing resistive film 104 to reversibly transition between a high-resistance state and a low-resistance state. Alternatively, the absolute value of the initial break voltage may be less than that of a write-in voltage. In this case, the initial break voltage may be repeatedly or continuously applied for a predetermined period. As illustrated in FIG. 1A, the application of the initial break voltage forms local region 105 being in contact with second electrode 106 and not in contact with first electrode 103.

Local region 105 is conceived to include a filament (conductive path) made up of oxygen defect sites. Local region 105 has a minute size matching with the filament necessary for a current to flow. The formation of the filament in local region 105 will be described using a percolation model.

The percolation model is based on a theory that a density of oxygen defect sites exceeding a threshold increases the probability of forming a connection of oxygen defect sites in an assumed random distribution of oxygen defect sites in local region 105.

In the percolation model, a filament is formed by connecting a plurality of oxygen defect sites in local region 105. A resistance change in resistive film 104 is caused through the generation and disappearance of the oxygen defect sites in local region 105.

Here, the term "oxygen defect" refers to that oxygen in a metal oxide is deficient compared to that in a metal oxide having a stoichiometric composition, and the term "density of oxygen defect sites" corresponds to the degree of oxygen deficiency. That is, the density of oxygen defect sites increases as the degree of oxygen deficiency becomes higher.

Local region 105 may be formed at only one location in one resistive film 104 of gas sensor 100. The number of local regions 105 formed in resistive film 104 can be determined by, for example, electron beam absorbed current (EBAC) analysis.

In the case where local region 105 is present in resistive film 104, when a voltage is applied between first electrode 103 and second electrode 106, the current flowing in resistive film 104 is concentrated in local region 105.

Local region 105 has a small size and therefore generates heat by, for example, a current of approximately several tens of microamperes flowing at the time of reading a resistance value of gas sensor 100. This heat generation causes a considerable increase in the temperature. The power consumption when a current of approximately several tens of microamperes flows is, for example, less than 0.1 mW.

In view of this, second electrode 106 is made of a metal (e.g., Pt) having a catalytic action, and local region 105 is formed in contact with second electrode 106. According to this structure, second electrode 106 is heated by the heat generation in local region 105, and hydrogen atoms are efficiently dissociated from hydrogen-containing gas.

When a target gas to be examined contains hydrogen-containing gas, hydrogen atoms are dissociated from the hydrogen-containing gas at second electrode 106, and the dissociated hydrogen atoms bond with oxygen atoms in local region 105, and as a result, the resistance value of local region 105 decreases.

Gas sensor 100 thus has characteristics of decreasing a resistance value between first electrode 103 and second electrode 106 when hydrogen-containing gas is brought into contact with second electrode 106. When a target gas to be examined is brought into contact with second electrode 106, such characteristics allow the detection of hydrogen-containing gas contained in the gas, by detecting a decrease in the resistance value between first electrode 103 and second electrode 106.

Note that whichever state local region 105 may be in, a high-resistance state or a low-resistance state, a decrease in the resistance value is caused by hydrogen-containing gas brought into contact with second electrode 106. Accordingly, the hydrogen-containing gas can be detected by gas sensor 100 whichever state, high or low, the resistive state of local region 105 may be. Nevertheless, in order to clearly detect a decrease in the resistance value, local region 105 may be electrically set to a high-resistance state prior to the use of gas sensor 100.

The details of gas sensor 100 for obtaining stable resistance change characteristics will now be described.

Resistive film 104 is made of an oxygen-deficient metal oxide. The mother metal of the metal oxide may be selected at least one from among aluminum (Al) and transition metals, such as tantalum (Ta), hafnium (Hf), titanium (Ti), zirconium (Zr), niobium (Nb), tungsten (W), nickel (Ni), and iron (Fe). Since transition metals have multiple oxidation states, it is possible to achieve different resistive states by a redox reaction.

Here, the term "oxygen-deficient metal oxide" refers to a metal oxide having a higher degree of oxygen deficiency compared to a metal oxide having a stoichiometric composition of the same metal elements. An oxygen-deficient metal oxide typically has semiconductor characteristics, whereas the metal oxide having the stoichiometric composition is typically an insulator. Gas sensor 100 having resistive film 104 made of an oxygen-deficient metal oxide can achieve high reproducibility and stable resistance change behavior.

For example, when the metal oxide constituting resistive film 104 is a hafnium oxide represented by $HfO_x$, where x is 1.6 or greater, a resistance value of resistive film 104 can be stably changed. In this case, the hafnium oxide film may have a thickness of 3 nm to 4 nm.

When the metal oxide constituting resistive film 104 is a zirconium oxide represented by $ZrO_x$, where x is 1.4 or greater, the resistance value of resistive film 104 can be stably changed. In this case, the zirconium oxide film may have a thickness of 1 nm to 5 nm.

When the metal oxide constituting resistive film 104 is a tantalum oxide represented by $TaO_x$, where x is 2.1 or greater, the resistance value of resistive film 104 can be stably changed.

The composition of each the above-mentioned metal-oxide layers can be measured by Rutherford backscattering spectrometry.

The materials for first electrode 103 and second electrode 106 are selected from, for example, among platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), titanium aluminum nitride (TiAlN), etc.

Specifically, second electrode 106 is constituted of a material having a catalytic action of dissociating hydrogen atoms from gas molecules including the hydrogen atoms, such as platinum (Pt), iridium (Ir) or palladium (Pd), or an alloy including at least one of these. First electrode 103 may be made of a material including at least one of tungsten (W), nickel (Ni), tantalum (Ta), titan (Ti), aluminum (Al), tantalum nitride (TaN), or titanium nitride (TiN), having a standard electrode potential lower than that of a metal constituting a metal oxide. A material having a higher value of the standard electrode potential is more difficult to be oxidized.

Substrate 101 may be any substrate and is, for example, a silicon single crystal substrate or a semiconductor substrate, but shall not be limited to such. Since resistive film 104 can be formed at a relatively low substrate temperature, resistive film 104 can also be formed, for example, on a resin material.

Gas sensor 100 may further include a load element electrically connected to resistive film 104, such as a fixed resistance, a transistor, or a diode.

Here, resistance change characteristics of gas sensor 100 exhibited due to voltage application will be described based on actual results obtained using a sample device. It should be noted that resistance change characteristics of gas sensor 100 exhibited due to hydrogen-containing gas will be mentioned later.

Figure 2:
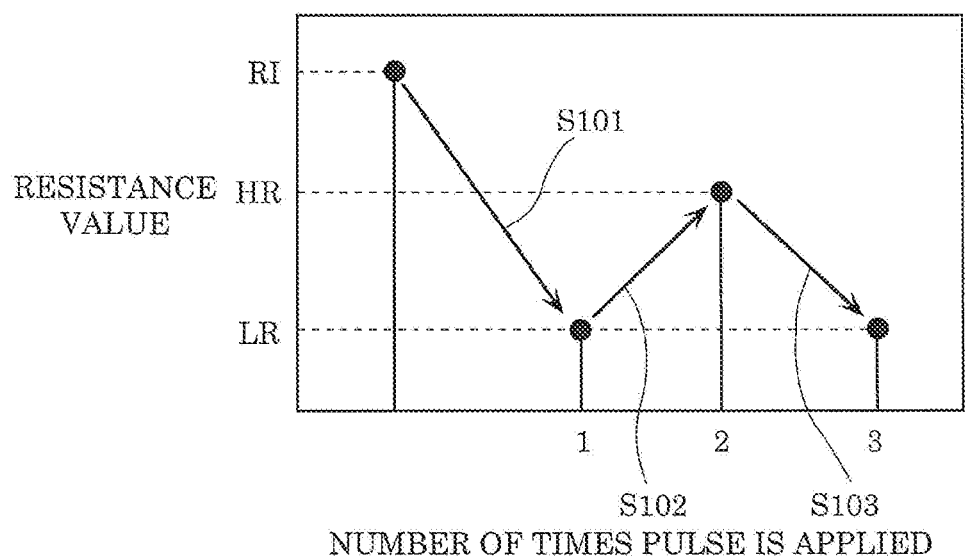
FIG. 2 illustrates an example of a state transition of the gas sensor according to Embodiment 1.

FIG. 2 is a graph showing resistance change characteristics actually measured using the sample device.

In gas sensor 100 as the sample device giving the measurement results shown in FIG. 2, the size of first electrode 103, second electrode 106, and resistive film 104 is defined as 0.5 μm×0.5 μm (area: 0.25 μm²). The value of y in $TaO_y$, representing the composition of a tantalum oxide constituting resistive film 104 is 2.47. Resistive film 104 has a thickness of 5 nm. In such gas sensor 100, when a read-out voltage (e.g., 0.4 V) is applied between first electrode 103 and second electrode 106, initial resistance value RI is approximately $10^7 \Omega$ to $10^8 \Omega$.

As illustrated in FIG. 2, when a resistance value of gas sensor 100 is initial resistance value RI (a value higher than resistance value HR in a high-resistance state), the application of an initial break voltage between first electrode 103 and second electrode 106 changes the resistance value to low resistance value LR (S101). Subsequently, when two different kinds of voltage pulses, i.e., a positive voltage pulse and a negative voltage pulse, having different polarities and each having a pulse width of 100 ns, are alternately applied as a write-in voltage between first electrode 103 and second electrode 106, a resistance value between first electrode 103 and second electrode 106 changes as illustrated in FIG. 2.

That is, when a positive voltage pulse (pulse width: 100 ns) is applied as the write-in voltage between the electrodes, the resistance value between first electrode 103 and second electrode 106 increases from low resistance value LR to high resistance value HR (S102). When a negative voltage pulse (pulse width: 100 ns) is applied as the write-in voltage between the electrodes, the resistance value between first electrode 103 and second electrode 106 decreases from high resistance value HR to low resistance value LR (S103). It should be noted that the polarity of a voltage pulse is "positive" when a potential of second electrode 106 is higher than that of first electrode 103 as a reference, and is "negative" when the potential of second electrode 106 is lower than that of first electrode 103 as a reference.

Figure 3:
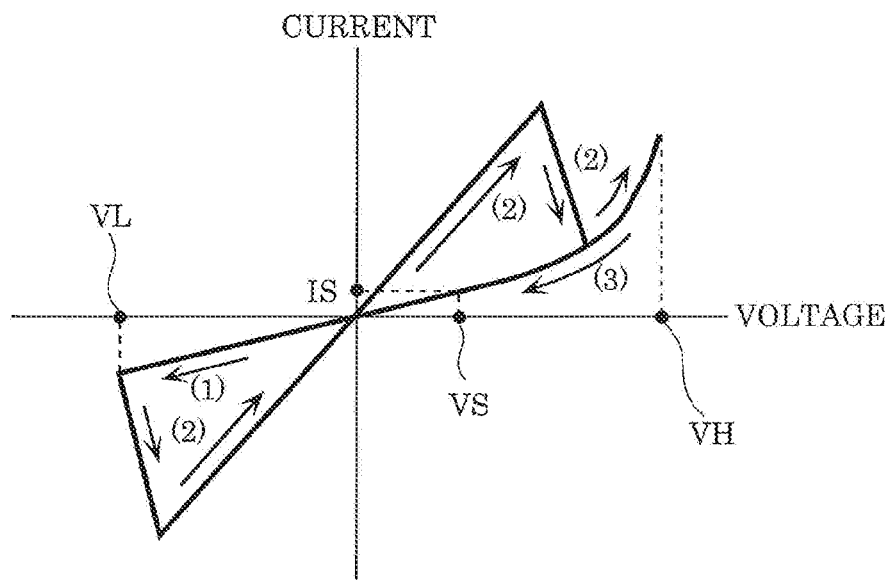
FIG. 3 illustrates an example of current-voltage characteristics of the gas sensor according to Embodiment 1.

FIG. 3 illustrates an example of current-voltage characteristics of gas sensor 100. FIG. 3 illustrates current-voltage characteristics obtained as a result of measuring a current that flows through gas sensor, while a changing voltage is applied between first electrode 103 and second electrode 106 of gas sensor 100. Specifically, gas sensor 100 was previously set to a high-resistance state, and then the applied voltage was changed: (1) firstly from zero to negative write-in voltage VL; (2) subsequently from negative write-in voltage VL to positive write-in voltage VH; and (3) lastly from positive write-in voltage VH to zero. The definitions of "positive" and "negative" in voltage are as described above.

When the applied voltage reaches a negative voltage having a predetermined value, the resistance value between first electrode 103 and second electrode 106 decreases from high resistance value HR to low resistance value LR (an absolute value of current increases). When the applied voltage reaches a positive voltage having a predetermined value, the resistance value between first electrode 103 and second electrode 106 increases from low resistance value LR to high resistance value HR (the absolute value of current decreases).

Note that in the application of the gas detection device to gas detection, a resistance value between first electrode 103 and second electrode 106 is measured according to detection current IS that flows when read-out voltage VS is applied between the electrodes.

Manufacturing Method and Operation of Gas Sensor

Next, an example of a method of manufacturing gas sensor 100 will be described with reference to FIGS. 4A through 4G.

Figure 4A:
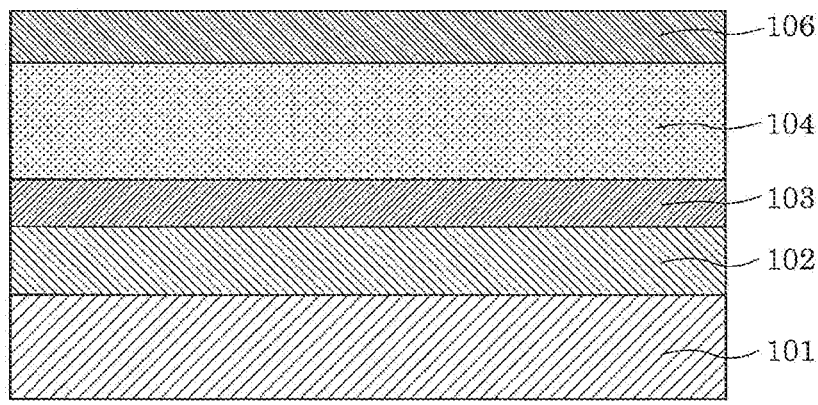
FIG. 4A is a cross-sectional view illustrating an example of a method of manufacturing the gas sensor according to Embodiment 1.

First, as illustrated in FIG. 4A, insulating film 102 having a thickness of 200 nm is formed on substrate 101, for example, of single crystal silicon, using a thermal oxidation method. Subsequently, first electrode 103, e.g., a Pt thin film having a thickness of 100 nm, is formed on insulating film 102 by sputtering. In addition, an adhesion layer of, for example, Ti and TiN may be formed between first electrode 103 and insulating film 102 by sputtering. Subsequently, an oxygen-deficient metal-oxide layer which becomes resistive film 104 is then formed on first electrode 103 by reactive sputtering using, for example, a Ta target. Resistive film 104 is thus formed.

If the thickness of resistive film 104 is too thick, a problem is that an initial resistance value becomes too high, etc., and if the thickness is too thin, it is a problem that a stable resistance change cannot be obtained. For the reasons stated above, the thickness of resistive film 104 may be about 1 nm or more and about 8 nm or less.

Next, second electrode 106 of, e.g., a Pt thin film having a thickness of 150 nm, is formed on resistive film 104 by sputtering.

Figure 4B:
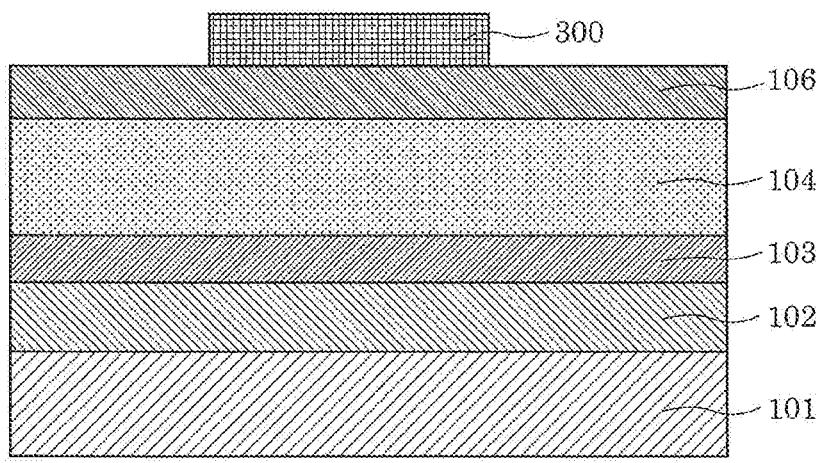
FIG. 4B is a cross-sectional view illustrating the example of the method of manufacturing the gas sensor according to Embodiment 1.
Figure 4C:
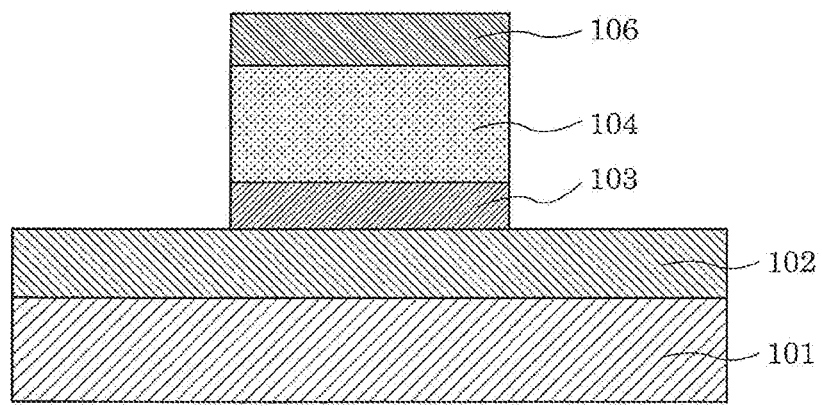
FIG. 4C is a cross-sectional view illustrating the example of the method of manufacturing the gas sensor according to Embodiment 1.

Next, photoresist mask 300 is subsequently formed by a photolithography process, as illustrated in FIG. 4B. Subsequently, first electrode 103, resistive film 104, and second electrode 106 are formed into the shape of a device by dry etching using mask 300, as illustrated in FIG. 4C.

Figure 4D:
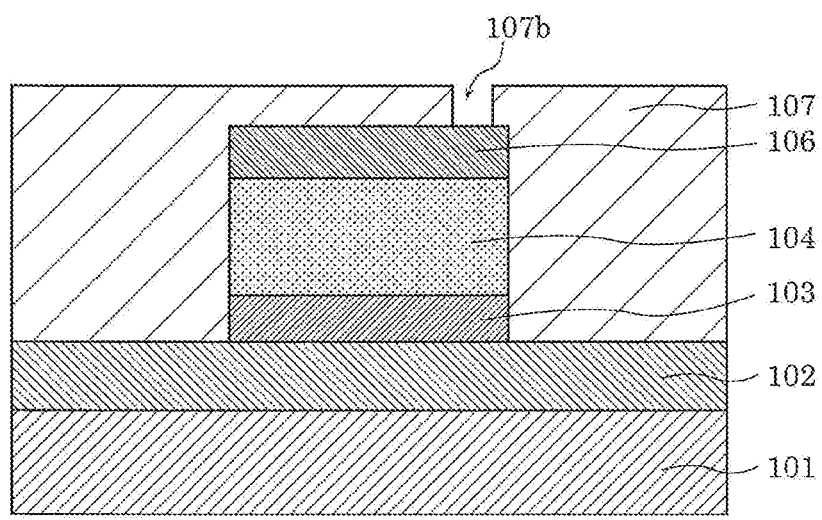
FIG. 4D is a cross-sectional view illustrating the example of the method of manufacturing the gas sensor according to Embodiment 1.

Subsequently, insulating film 107 is formed to cover insulating film 102, first electrode 103, resistive film 104, and second electrode 106, as illustrated in FIG. 4D. Via hole 107b reaching a portion of the main surface of second electrode 106 is then formed by etching insulating film 107.

Figure 4E:
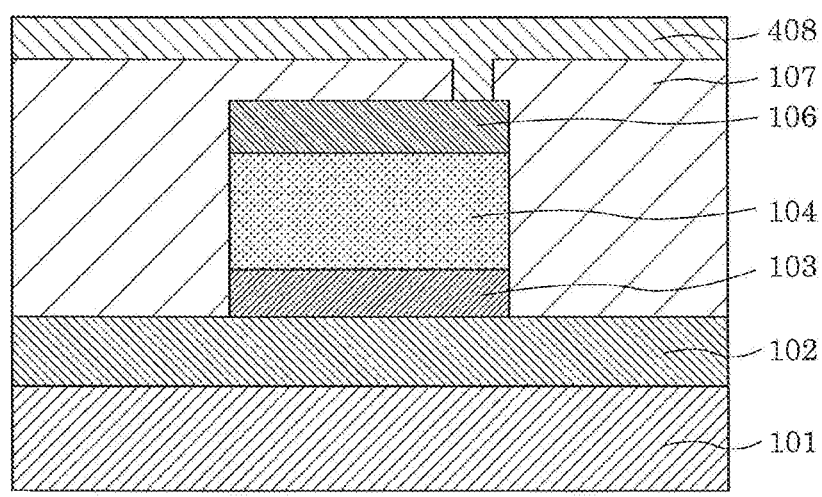
FIG. 4E is a cross-sectional view illustrating the example of the method of manufacturing the gas sensor according to Embodiment 1.
Figure 4F:
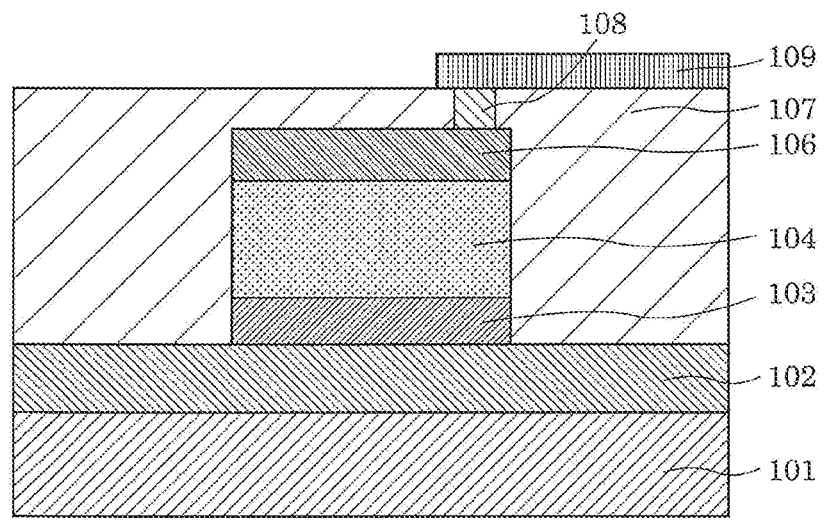
FIG. 4F is a cross-sectional view illustrating the example of the method of manufacturing the gas sensor according to Embodiment 1.

Next, conductive film 408 is formed on the main surface of insulating film 107 and inside of via hole 107b to fill via hole 107b, as illustrated in FIG. 4E. Subsequently, conductive film 408 on insulating film 107 is removed by chemical mechanical polishing (CMP) to form via 108 in via hole 107b, as shown in FIG. 4F. Another conductive film is further formed on insulating film 107 and is patterned to form wiring 109 connected to via 108.

Figure 4G:
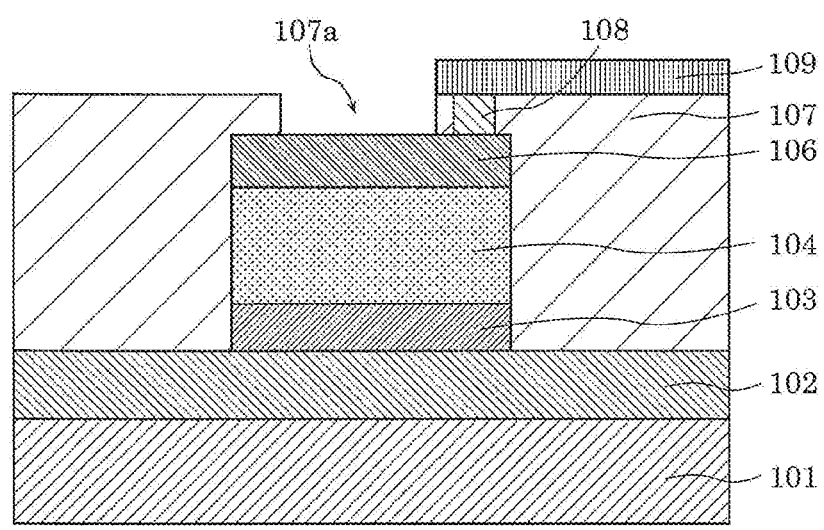
FIG. 4G is a cross-sectional view illustrating the example of the method of manufacturing the gas sensor according to Embodiment 1.

Next, opening 107a that exposes part of the main surface of second electrode 106 by etching insulating film 107, as shown in FIG. 4G.

Subsequently, an initial break voltage is applied between first electrode 103 and second electrode 106 to form local region 105 illustrated in FIG. 1A in resistive film 104. Gas sensor 100 is thus manufactured.

Variation of Gas Sensor

Figure 5:
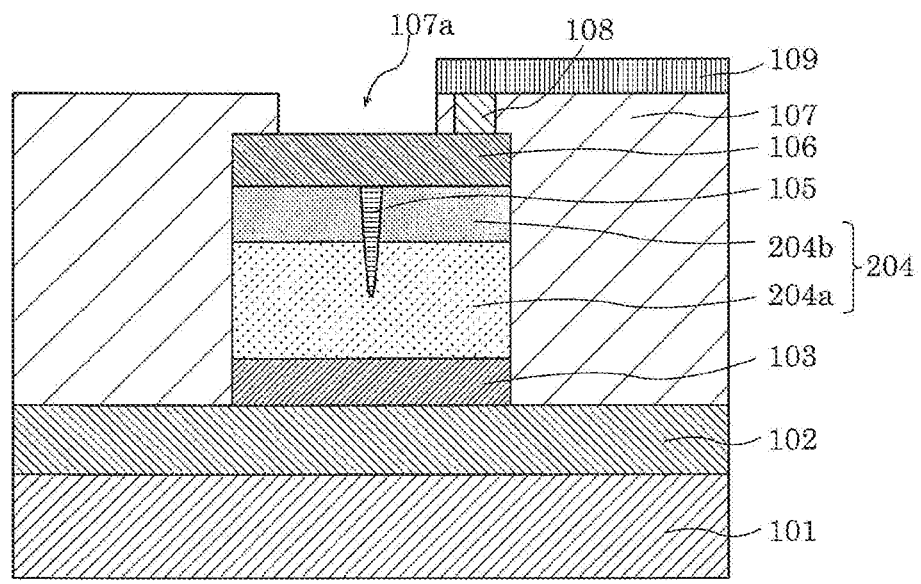
FIG. 5 is a cross-sectional view illustrating a gas sensor according to a variation of Embodiment 1.

FIG. 5 is a cross-sectional view illustrating an example of a structure of a gas sensor according to a variation of Embodiment 1. The following describes the gas sensor according to this variation, focusing only on the points different from gas sensor 100 of Embodiment 1.

Gas sensor 200 of this variation is different from gas sensor 100 of Embodiment 1 in that resistive film 204 includes two layers of first metal-oxide layer 204a that is in contact with first electrode 103 and second metal-oxide layer 204b that is in contact with second electrode 106. Note that resistive film 204 is not limited to a layered product of two metal-oxide layers and may be a layered product of three or more metal-oxide layers.

First metal-oxide layer 204a and second metal-oxide layer 204b include local region 105 in which a degree of oxygen deficiency reversibly changes depending on the application of an electrical pulse and in response to hydrogen-containing gas. Local region 105 penetrates at least through second metal-oxide layer 204b to be in contact with second electrode 106.

Stated differently, resistive film 204 has at least a layered structure composed of first metal-oxide layer 204a containing a first metal oxide and second metal-oxide layer 204b containing a second metal oxide. First metal-oxide layer 204a is disposed between first electrode 103 and second metal-oxide layer 204b, and second metal-oxide layer 204b is disposed between first metal-oxide layer 204a and second electrode 106.

Second metal-oxide layer 204b may have a thickness less than that of first metal-oxide layer 204a. In this case, a structure including local region 105 that is not in contact with first electrode 103 can be readily formed. A degree of oxygen deficiency of second metal-oxide layer 204b may be lower than that of first metal-oxide layer 204a. In this case, a resistance value of second metal-oxide layer 204b is higher than that of first metal-oxide layer 204a. Accordingly, most of the voltage applied to resistive film 204 is applied to second metal-oxide layer 204b. This structure is advantageous, for example, for concentrating an initial break voltage in second metal-oxide layer 204b and reducing an initial break voltage necessary for forming local region 105.

In the present disclosure, when a metal constituting first metal-oxide layer 204a is the same as that constituting second metal-oxide layer 204b, the term "degree of oxygen content" may be used instead of the term "oxygen deficiency". "High oxygen content" corresponds to "low degree of oxygen deficiency" and "low oxygen content" corresponds to "high degree of oxygen deficiency".

However, as described below, resistive film 204 according to this embodiment is not limited to the case where the metal constituting first metal-oxide layer 204a is the same as that constituting second metal-oxide layer 204b, and the metals may be different from each other. That is, first metal-oxide layer 204a and second metal-oxide layer 204b may be made of different metal oxides.

When the first metal constituting first metal-oxide layer 204a and the second metal constituting second metal-oxide layer 204b are the same, an oxygen content has a corresponding relationship with a degree of oxygen deficiency. That is, when the oxygen content of the second metal oxide is higher than that of the first metal oxide, the second metal oxide has a degree of oxygen deficiency lower than that of the first metal oxide.

Resistive film 204 includes local region 105 in the vicinity of an interface between first metal-oxide layer 204a and second metal-oxide layer 204b. Local region 105 has a degree of oxygen deficiency higher than that of second metal-oxide layer 204b, and is different from that of first metal-oxide layer 204a.

Local region 105 is formed in resistive film 204 by the application of an initial break voltage between first electrode 103 and second electrode 106. The initial break voltage forms local region 105 that is in contact with second electrode 106, penetrates through second metal-oxide layer 204b, partially penetrates into first metal-oxide layer 204a, and is not in contact with first electrode 103.

One example of an evaluation on the resistance change characteristics, of thus-structured gas sensor 200, which exhibit in response to hydrogen-containing gas will be described.

Figure 6:
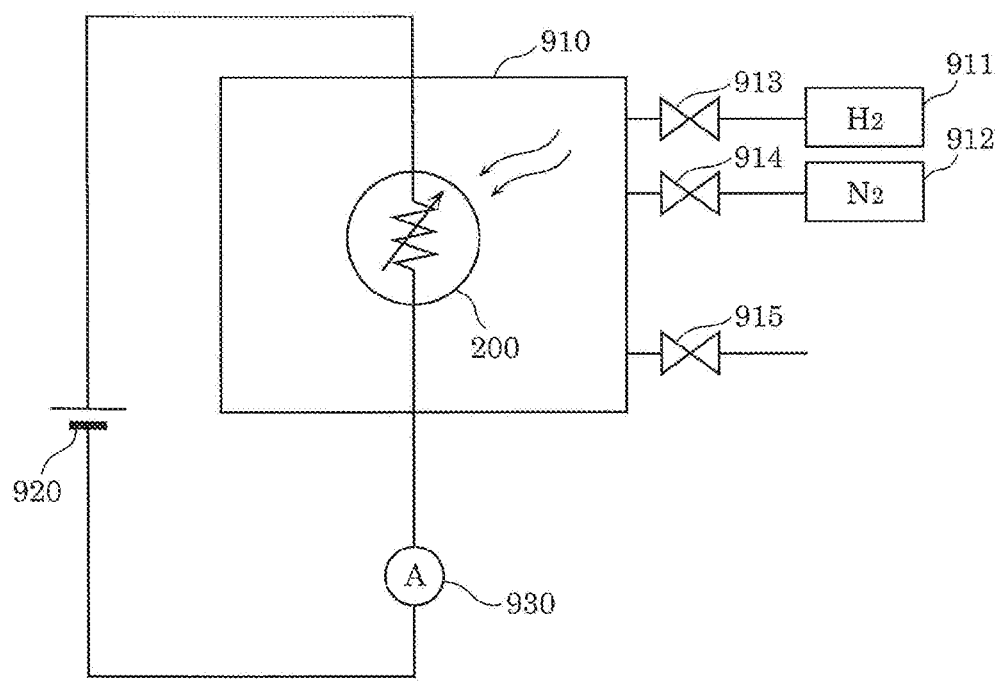
FIG. 6 illustrates a system for evaluating the gas sensor according to the variation of Embodiment 1.

FIG. 6 is a block diagram illustrating an example of an evaluation system used for evaluating gas sensor 200. Evaluation system 900 illustrated in FIG. 6 includes airtight container 910 accommodating gas sensor 200, detection power source 920 that generates a detection voltage, and current meter 930. Airtight container 910 is connected to hydrogen cylinder 911 and nitrogen cylinder 912 through introduction valves 913 and 914, respectively, and gas inside airtight container 910 can be exhausted through exhaust valve 915.

Figure 7:
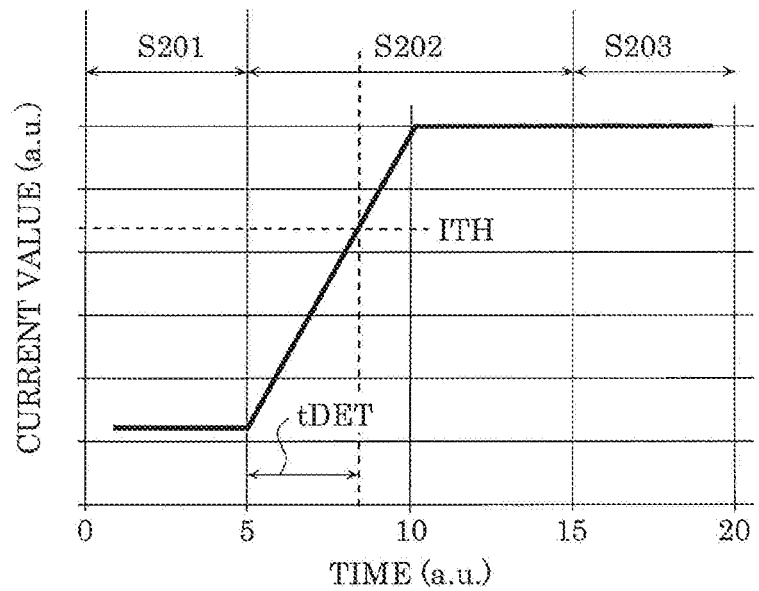
FIG. 7 illustrates a result of an evaluation on the gas sensor according to the variation of Embodiment 1.

FIG. 7 is a graph illustrating one example of an evaluation on gas sensor 200. The horizontal axis indicates time (a.u.) while the vertical axis indicates the value of a current (a.u.) flowing through gas sensor 200. In the experiment, nitrogen gas was introduced into airtight container 910 accommodating gas sensor 200, and a detection voltage was applied to start measurement of the current. Subsequently, hydrogen gas was introduced into airtight container 910, and after a predetermined period of time, the introduction gas was changed from hydrogen gas to nitrogen gas.

FIG. 7 shows a result of the experiment. The horizontal axis indicates three periods: the former process of nitrogen introduction (Step S201); the introduction of hydrogen (Step S202); and the latter process of nitrogen introduction (Step S203). The current value started to increase after the change of the introduction gas from nitrogen gas to hydrogen gas, and since the current value reaches a predetermined threshold current ITH, hydrogen gas is detected. The time from when the current value increases after the start of the introduction of hydrogen gas until when the current value reaches the predetermined threshold current is presented as hydrogen detection time tDET. After the detection of hydrogen, the current value increases even more and then saturates.

After the detection of the hydrogen gas, the current value remained saturated even after the introduction gas was changed from hydrogen gas to nitrogen gas, and did not decrease again. In other words, it is observable that gas sensor 200 has such characteristics that a resistance value between first electrode 103 and second electrode 106 decreases when gas (hydrogen gas in this case) containing hydrogen molecules including hydrogen atoms is brought into contact with second electrode 106, and the state in which the resistance value stays low is maintained even when gas (nitrogen gas in this case) not including hydrogen atoms is brought into contact with second electrode 106 after the decrease.

In this evaluation example, a predetermined voltage (reset voltage) was applied between first electrode 103 and second electrode 106 to set local region 105 to a high-resistance state prior to the use of gas sensor 200.

In the operation of monitoring for hydrogen-containing gas, a detection voltage of 0.6 V was applied between first electrode 103 and second electrode 106, hydrogen gas was detected, and in the state where the current value saturated, a current of approximately 20 µA flowed between first electrode 103 and second electrode 106.

It is therefore demonstrated that gas sensor 200 is capable of monitoring for hydrogen-containing gas with a very low power consumption of 0.012 mW at the highest. The voltage of 0.6 V may be applied at all times between first electrode 103 and second electrode 106.

When a detection voltage of 0.4 V was applied between first electrode 103 and second electrode 106, a resistance change did not occur in response to hydrogen gas, and thereby, hydrogen gas was not detected. This was probably caused because the amount of heat generated in local region 105 by the application of the detection voltage of 0.4 V was not sufficient to accelerate the catalytic action of second electrode 106. It is inferred that the application of a detection voltage of 0.6 V was necessary to detect hydrogen gas.

The detection voltage of 0.6 V in this case is one example of a detection voltage that activates the characteristic such that when second electrode 106 comes into contact with gas containing gas molecules including hydrogen atoms, a resistance value between first electrode 103 and second electrode 106 decreases.

The detection voltage here is read-out voltage VS illustrated in FIG. 3. It is necessary to prevent the resistance value of gas sensor 200 from changing due to a cause other than hydrogen atoms. As illustrated in FIG. 3, when a positive voltage having a predetermined value is applied to gas sensor 200, the resistance value of gas sensor 200 changes from low to high resistance, whereas when a negative voltage having a predetermined value is applied to gas sensor 200, the resistance value of gas sensor 200 changes from high to low resistance. This is why an absolute value of a detection voltage (read-out voltage VS) has to be set to a value less than a predetermined value so as not to cause a change in the resistance value of gas sensor 200.

After gas sensor 200 detects hydrogen gas and the current value increases and then saturates, the current value does not decrease again even the concentration of hydrogen gas decreases. Therefore, in order to change the state of gas sensor 200 back to a high-resistance state which is a state before the detection of hydrogen gas, a positive voltage (reset voltage) having a predetermined value needs to be applied again between first electrode 103 and second electrode 106.

Based on the results described above, the inventors presume a mechanism of detecting hydrogen-containing gas by gas sensor 200 as follows.

When hydrogen-containing gas is brought into contact with second electrode 106, hydrogen atoms are dissociated from the hydrogen-containing gas by the catalytic action of second electrode 106. The dissociated hydrogen atoms diffuse in second electrode 106 for maintaining the equilibrium state, and reach local region 105.

The hydrogen atoms that have reached local region 105 cause a reduction reaction in minute local region 105, and thus, oxygen in local region 105 and the hydrogen atoms react with each other. Oxygen deficiency newly occurs in local region 105 and the degree of oxygen deficiency in local region 105 increases. Oxygen deficiency occurs in many places in local region 105; as a result, filaments formed from such oxygen deficiencies are readily connected to one another to reduce a resistance value of local region 105. As a result, the current flowing between first electrode 103 and second electrode 106 increases.

It is inferable that the above-described behavior is not limited to gas sensor 200 and also exhibits in gas sensor 100 or any other gas sensor having substantially the same structures of the main sections as those of the main sections of gas sensor 200. It is also inferable that detectable gas is not limited to hydrogen gas, and the above-described behavior also exhibits in detecting various kinds of hydrogen-containing gas such as methane or alcohol.

As described above, according to the gas sensor of this embodiment, it is possible to attain a gas sensor highly capable of saving power, which generates heat only with a current for detecting the resistive state of the gas sensor, and is capable of detecting hydrogen-containing gas without heating with a separate heater.

In addition, when gas containing gas molecules including hydrogen atoms is brought into contact with the second electrode, a resistance value between the first electrode and the second electrode decreases, and even when gas not including hydrogen atoms is brought into contact with the second electrode after the decrease, it is possible to maintain the state in which the resistance value stays low.

Gas Detection Device

Figure 8A:
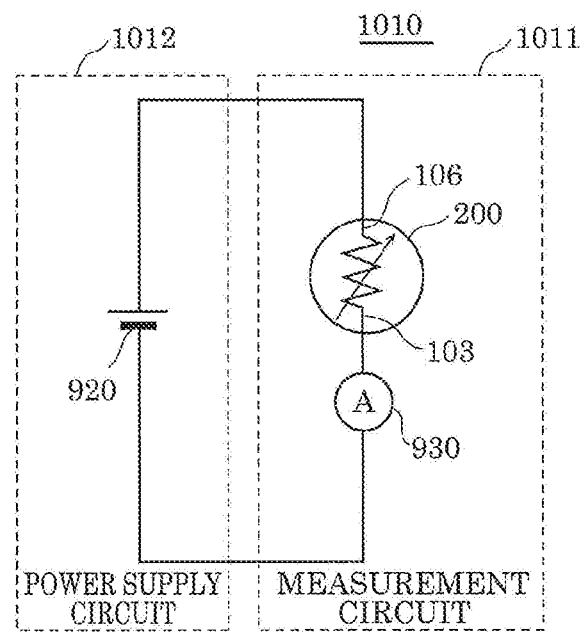
FIG. 8A is a circuit diagram illustrating an example of a gas detection device according to Embodiment 1.

FIG. 8A is a circuit diagram illustrating an example of gas detection device 1010 including gas sensor 200 according to the variation of Embodiment 1.

Gas detection device 1010 includes measurement circuit 1011 formed by connecting gas sensor 200 and current meter 930 in series, and power supply circuit 1012 including detection power source 920. Power supply circuit 1012 may be a conversion circuit that converts, into a desired voltage, a supply voltage provided from internal batteries or an external source. Here, a total body of measurement circuit 1011 and power supply circuit 1012, which excludes gas sensor 200, is one example of a drive circuit that applies a predetermined voltage to a gas sensor.

More specifically, second electrode 106 of gas sensor 200 is connected to a positive potential terminal of detection power source 920 via 108 and wiring 109 illustrated in FIG. 5. First electrode 103 of gas sensor 200 is connected to one end of current meter 930 via, for example, a wiring (not shown in the diagram) or the like. The other end of current meter 930 is connected to a negative potential terminal of detection power source 920. According to the above-described structure, a predetermined voltage is applied between first electrode 103 and second electrode 106 of gas sensor 200, by detection power source 920.

In gas detection device 1010, a time point at which a current value measured by current meter 930 connected to gas sensor 200 exceeds predetermined threshold current ITH illustrated in FIG. 7 is a point of determination for hydrogen detection. That is, gas detection device 1010 determines that hydrogen is detected at the time point when the current flowing through gas sensor 200 exceeds predetermined threshold current ITH.

As described above, with the gas sensor of the present embodiment, it is possible to detect hydrogen with less power. Note that although the present embodiment has described the results of the experiment in the case of detecting hydrogen gas, it is observed that the same effects can be achieved in the case of detecting hydrogen-containing gas (e.g., ammonia gas).

The above has illustrated an example of detecting hydrogen, and the gas sensor of this embodiment not only detects hydrogen but also has the characteristics of maintaining the state in which hydrogen is detected (a high-resistance state is maintained even when hydrogen concentration decreases). Accordingly, it is also effective to provide in advance, in a hydrogen plant or the like, a plurality of the gas sensors according to the present embodiment as hydrogen leak storage elements for examining whether there have been hydrogen leaks in the past.

Gas Detection Device Having a Reset Function

Figure 8B:
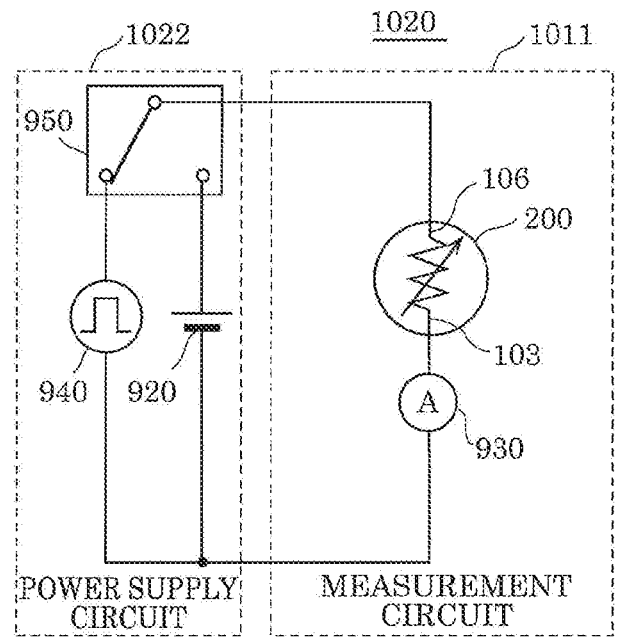
FIG. 8B is a circuit diagram illustrating an example of the gas detection device according to Embodiment 1.

FIG. 8B is a circuit diagram illustrating an example of a gas detection device capable of resetting gas sensor 200 from a low-resistance state to a high-resistance state. To configure gas detection device 1020 in FIG. 8B, power supply circuit 1012 in gas detection device 1010 illustrated in FIG. 8A is changed to power supply circuit 1022 in which switch 950 and reset power source 940 are added to detection power source 920.

Here, power supply circuit 1022 may be a conversion circuit that converts, into a desired voltage, a supply voltage provided from internal batteries or an external source. A total body of measurement circuit 1011 and power supply circuit 1022, which excludes gas sensor 200, is one example of a drive circuit that applies a predetermined voltage to a gas sensor.

Having detected hydrogen-containing gas using gas sensor 200 and current meter 930, gas detection device 1020 connects switch 950 to reset power source 940. With the application of a reset voltage (e.g., 1.5 V) to gas sensor 200 by reset power source 940, gas sensor 200 that has been in a low-resistance state due to hydrogen-containing gas is reset to a high-resistance state. The reset voltage here is write-in voltage VH illustrated in FIG. 3.

Thus, by resetting gas sensor 200, which has been in a low-resistance state after the detection of hydrogen-containing gas, to a high-resistance state, gas sensor 200 becomes capable of repeatedly detecting hydrogen-containing gas.

It should be noted that the effects achieved with the aforementioned gas detection devices 1010 and 1020 can be achieved not only in the case of using gas sensor 200 but also in the case of using gas sensor 100 or any other gas sensor having substantially the same structures of the main sections as those of the main sections of gas sensor 200.

The timing at which a reset voltage is applied between the first electrode and the second electrode to reset the gas sensor to a high-resistance state is not limited to timing after the detection of hydrogen-containing gas. For example, the gas sensor may be reset before the detection of hydrogen-containing gas (particularly before the first detection). Thus, by detecting hydrogen-containing gas using a gas sensor whose resistive state is a high-resistance state, it is possible to more clearly detect a decrease in a resistance value between the electrodes. This therefore enhances the gas sensor's capability of detecting hydrogen-containing gas.

Gas Detection Device Having Refreshing Function

Figure 8C:
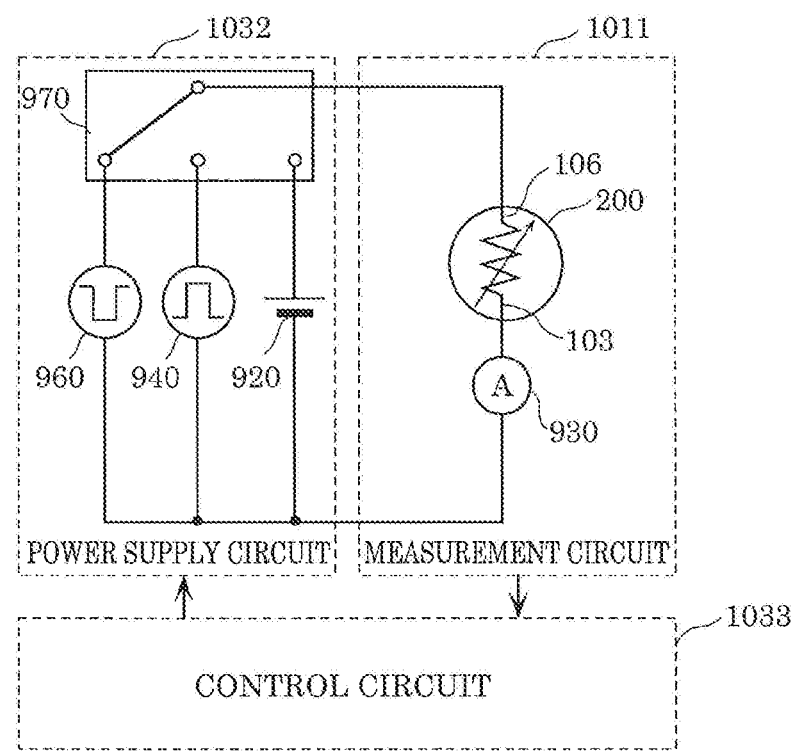
FIG. 8C is a circuit diagram illustrating an example of the gas detection device according to Embodiment 1.

FIG. 8C is a circuit diagram illustrating an example of a gas detection device capable of refreshing the resistive state of gas sensor 200 to a predetermined resistive state. Power supply circuit 1022 in gas detection device 1020 illustrated in FIG. 8B is changed to power supply circuit 1032, and control circuit 1033 is added to the configuration of gas detection device 1020 to configure gas detection device 1030 in FIG. 8C.

Power supply circuit 1032 includes switch 970, and additionally includes set power source 960, compared with power supply circuit 1022.

Control circuit 1033 is a logic circuit that controls a refreshing operation performed by gas detection device 1030.

Here, power supply circuit 1032 may be a conversion circuit that converts, into a desired voltage, a source voltage provided from an internal battery or an external source. A total body of measurement circuit 1011, power supply circuit 1032, and control circuit 1033, which excludes gas sensor 200, is one example of a drive circuit that applies a predetermined voltage to a gas sensor.

Figure 9A:
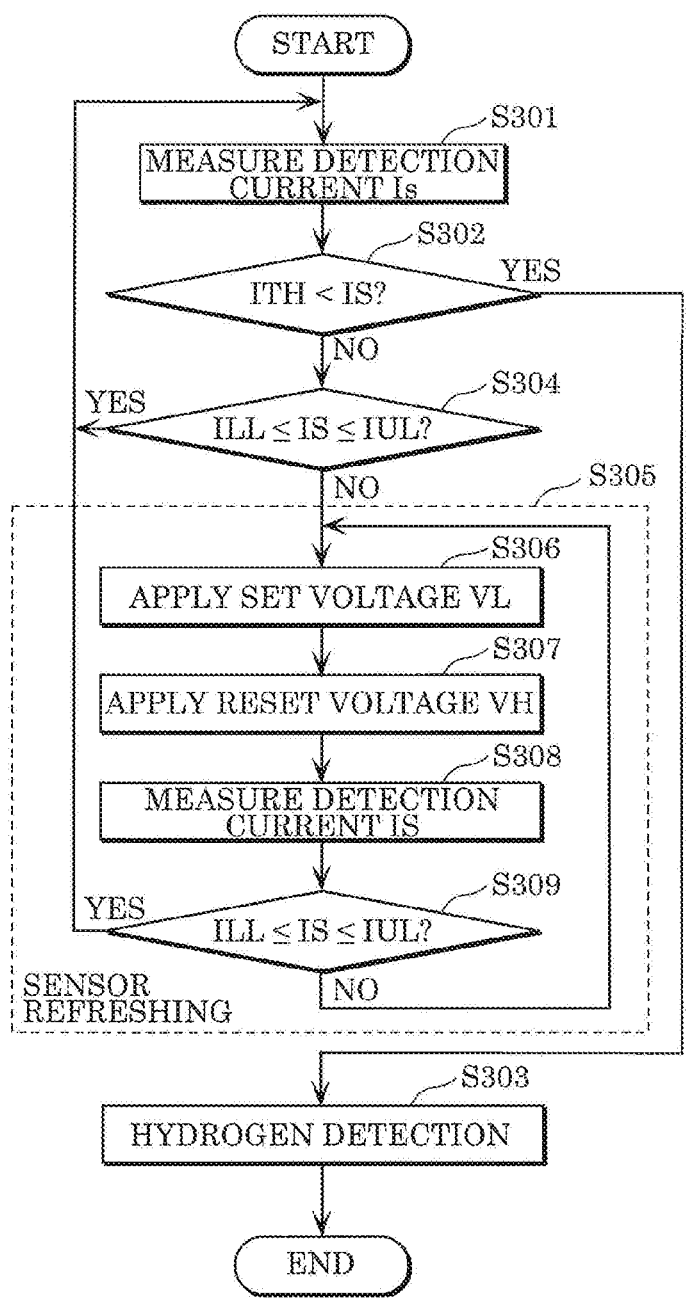
FIG. 9A is a flowchart illustrating an example of a hydrogen detection method according to Embodiment 1.

FIG. 9A is a flowchart illustrating an example of a gas detection operation performed by gas detection device 1030. Gas detection device 1030 operates, for example, in accordance with the flowchart in FIG. 9A under the control of control circuit 1033, as follows.

Measurement circuit 1011 measures detection current IS (S301).

Control circuit 1033 compares detection current IS with threshold current ITH, and when detection current IS is greater than threshold current ITH (YES in S302), determines that hydrogen-containing gas has been detected (S303).

When detection current IS is less than or equal to threshold current ITH (NO in S302), control circuit 1033 determines whether detection current IS is within a predetermined range. The predetermined range is a range for determining whether gas sensor 200 needs to be refreshed, and is set within a range of current values less than threshold current ITH. That is, ILL<IUL<ITH, where ILL denotes the lower limit and IUL denotes the upper limit of the predetermined range.

The predetermined range is one example of presenting, by a range for a detection current, a predetermined range for resistive film 204 (i.e., metal-oxide layer) before hydrogen-containing gas is brought into contact with second electrode 106 of gas sensor 200.

When detection current IS is within the predetermined range, that is, ILL≤IS≤IUL (YES in S304), gas detection device 1030 returns to step S301 and continues monitoring for hydrogen-containing gas. When detection current IS is outside the predetermined range (NO in S304), sensor refreshing is executed by the application of a predetermined voltage (S305).

In the sensor refreshing, switch 970 is connected to set power source 960, a set voltage is applied to gas sensor 200 from set power source 960, and gas sensor 200 is electrically set to a low-resistance state. The set voltage here is write-in voltage VL illustrated in FIG. 3 (S306).

Subsequently, switch 970 is connected to reset power source 940, a reset voltage is applied to gas sensor 200 from reset power source 940, and gas sensor 200 is electrically reset to a high-resistance state. The reset voltage here is write-in voltage VH illustrated in FIG. 3 (S307).

A pair of a set voltage and a reset voltage is one example of a predetermined voltage in sensor refreshing.

After the application of the set voltage and the reset voltage as a pair, whether refreshing is properly performed is verified. Specifically, gas detection device 1030 measures detection current IS (S308), and when detection current IS is within the above-described predetermined range (YES in S309), returns to step S301 and continues monitoring for hydrogen-containing gas. When detection current IS is still outside the predetermined range (NO in S309), sensor refreshing is executed again (S305).

In this way, gas detection device 1030 executes a process of applying a predetermined voltage (e.g., a pair of a set voltage and a reset voltage) between first electrode 103 and second electrode 106 of gas sensor 200 and subsequently measuring a resistance value (detection current IS) until the measured resistance value (detection current IS) falls within the predetermined range.

Note that in the sensor refreshing, unless a measured resistance value (detection current IS) falls within the predetermined range after the application of a predetermined voltage and the verification of a refreshing process are carried out up to a predetermined number of times, it may be determined that the restoration of the resistance value (i.e., sensor refreshing) failed. In other words, an upper limit may be set for a repeat count in the sensor refreshing.

Figure 9B:
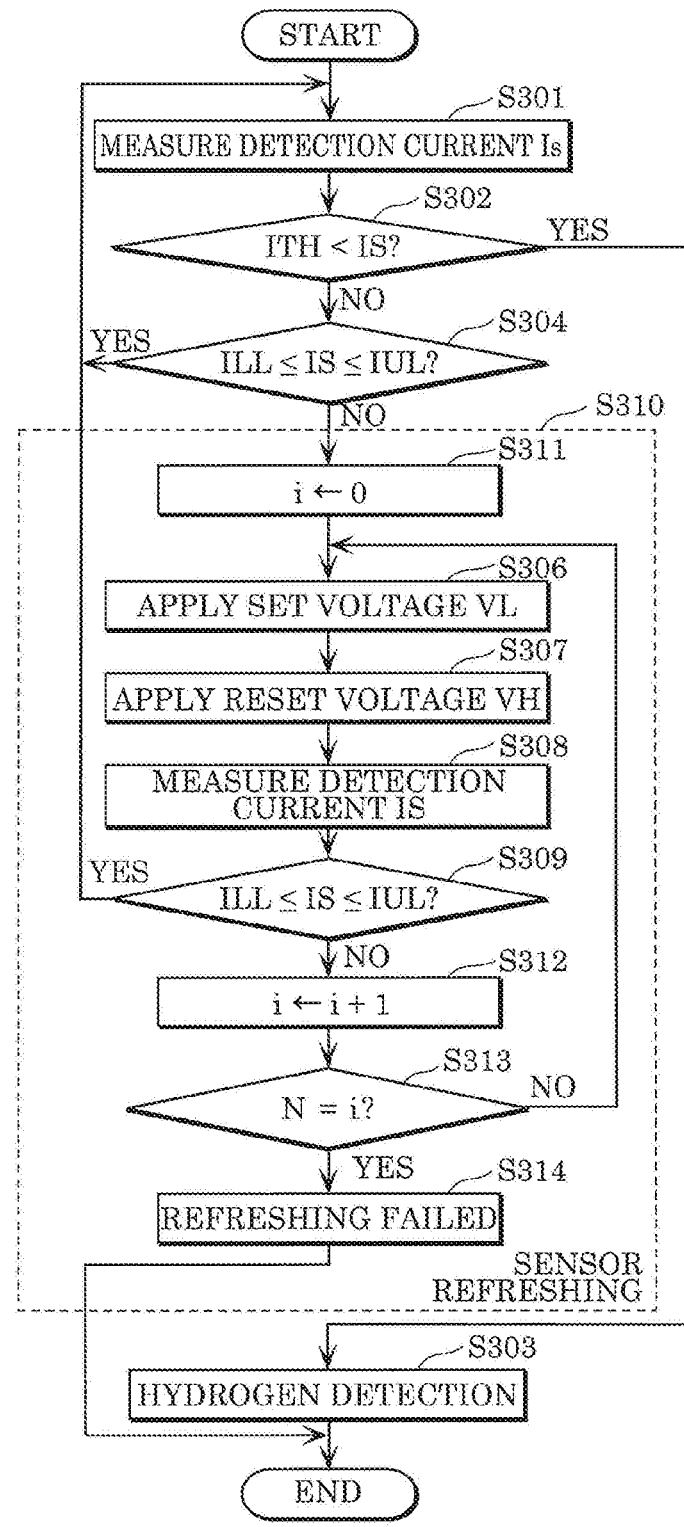
FIG. 9B is a flowchart illustrating an example of the hydrogen detection method according to Embodiment 1.

FIG. 9B is a flowchart illustrating an example of a gas detection operation in which an upper limit is set for a repeat count. In the flowchart in FIG. 9B, sensor refreshing (S310) is changed as follows, compared with the flowchart in FIG. 9A.

In the sensor refreshing (S310), repeat counter i is initialized (S311). After the application of the set voltage and the reset voltage as a pair (S306, S307), when detection current IS does not fall within the predetermined range (S308, No in S309), repeat counter i is incremented (S312).

When repeat counter i does not reach upper limit N for the repeat count (NO in S313), gas detection device 1030 returns to step S306 and carries out again the application of the set voltage and the reset voltage as a pair and the measurement of a resistance value (detection current IS).

When repeat counter i reaches upper limit N for the repeat count (YES in S313), it is determined that refreshing failed (S314).

According to the gas detection operation in FIG. 9B, through the failure in refreshing, it is possible to detect a breakdown or a lifespan of gas sensor 200 and handle with it by exchanging devices, etc. at the right time.

Figure 10:
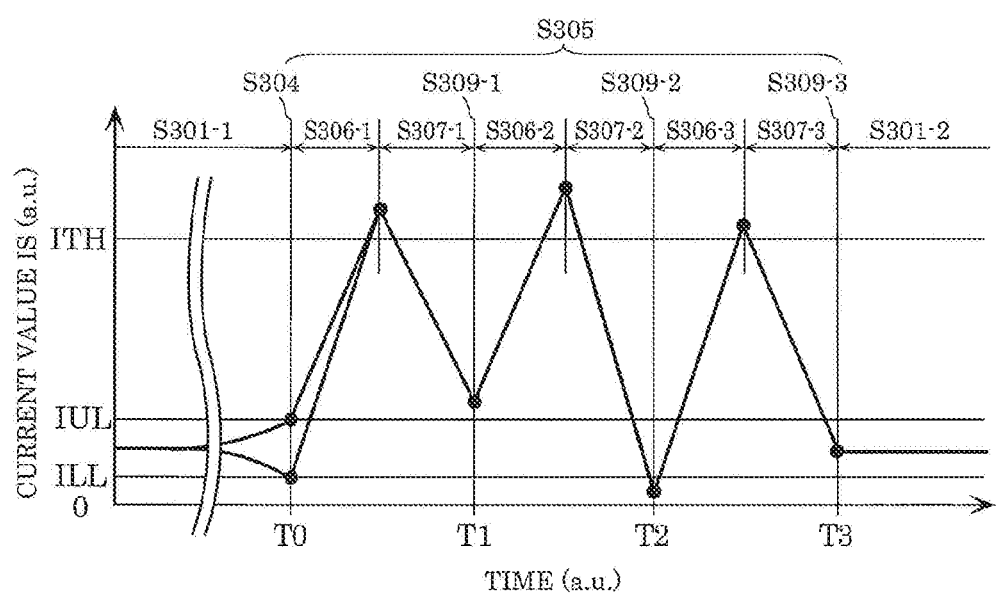
FIG. 10 illustrates an example of a refreshing operation performed using the hydrogen detection method according to Embodiment 1.

FIG. 10 is a graph illustrating a concrete example of a refreshing operation performed by gas sensor 200 in gas detection device 1030. The graph in FIG. 10 presents the resistive state of gas sensor 200 by detection currents IS that are measured. Reference signs used in the description below correspond, for example, to the step numbers in the flowchart in FIG. 9A, and the last number in a reference sign presents the number of times a loop process is executed.

Before time T0, gas detection device 1030 monitors for hydrogen-containing gas through the measurement of detection current IS (S301-1). Detection current IS is within the aforementioned predetermined range, that is, a range specified by lower limit ILL and upper limit IUL. In the following description, the predetermined range is also referred to as a normal range for the sake of explanation.

During the monitoring for hydrogen-containing gas, a characteristic fluctuation may occur in gas sensor 200 in some cases. The characteristic fluctuation is caused, for example, by the degradation of a sensor element or disturbance, and appears as a deviation from a normal range for detection current IS.

When detection current IS is detected as being greater than upper limit IUL or less than lower limit ILL (S304), the first loop of sensor refreshing (S305) is started (Time T0).

A set current and a reset current are applied in this order (S306-1, S307-1), and detection current IS is subsequently measured (S309-1). Here, since detection current IS has deviated from the normal range and is above upper limit IUL (IUL<IS), the second loop of sensor refreshing (S305) is started (time T1).

The set current and the reset current are applied in this order (S306-2, S307-2), and detection current IS is subsequently measured (S309-2). Here, since detection current IS has deviated from the normal range and is below lower limit ILL (IS<ILL), the third loop of sensor refreshing (S305) is started (time T2).

The set current and the reset current are applied in this order (S306-3, S307-3), and detection current IS is subsequently measured (S309-3). Here, since detection current IS has fallen within the normal range (ILL<IS<IUL), gas detection device 1030 restarts the monitoring for hydrogen-containing gas (S301-2).

In this way, gas detection device 1030 is capable of continuing the monitoring for hydrogen-containing gas while restoring the characteristic fluctuation of gas sensor 200 according to the deviation of detection current IS from a normal range.

Embodiment 2

A gas sensor system according to Embodiment 2 includes a gas detection device and an access device, and carries out each operation of hydrogen-containing gas detection, reset, and refreshing performed by the gas detection device based on wireless signals and wireless power provided from the access device.

Figure 11:
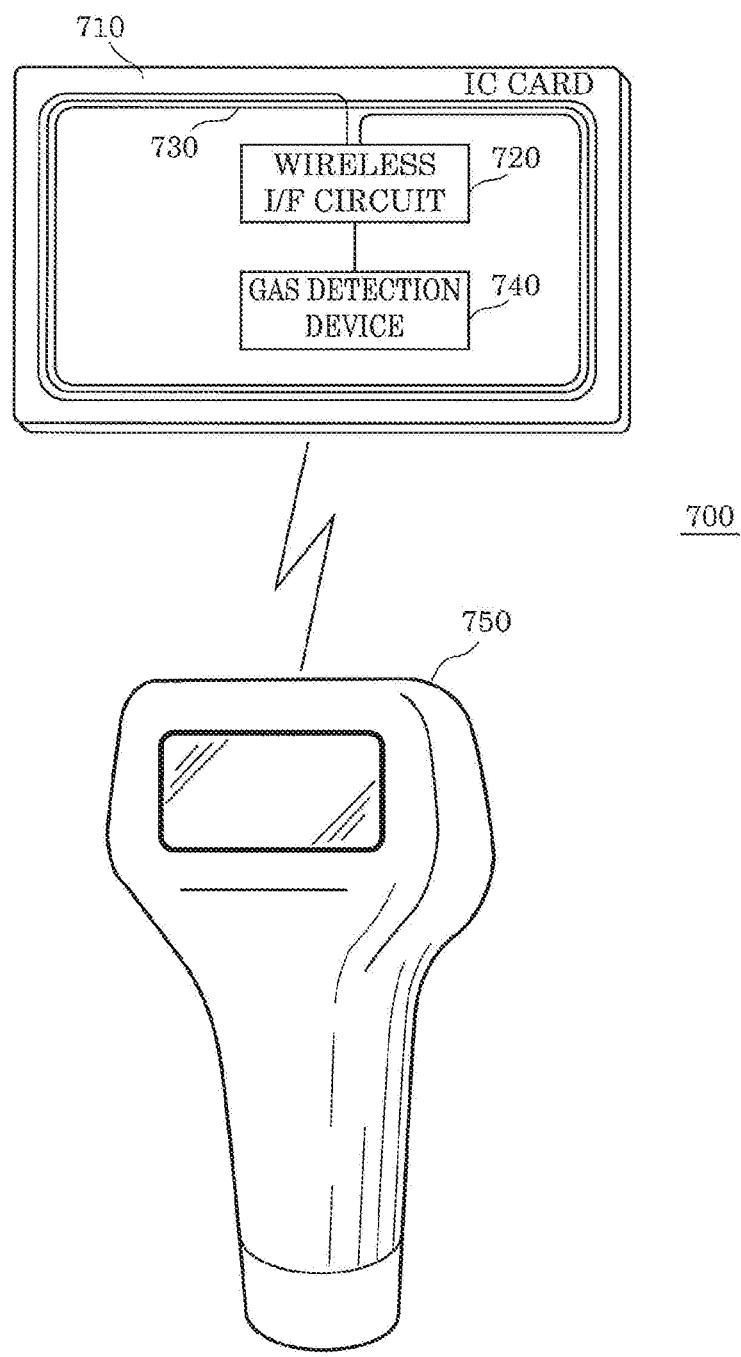
FIG. 11 is a pattern diagram illustrating an example of a configuration of a gas sensor system according to Embodiment 2.

FIG. 11 is a pattern diagram illustrating an example of a configuration of gas sensor system 700 according to Embodiment 2. As illustrated in FIG. 11, gas sensor system 700 includes IC card 710 and reader/writer 750 that is one example of the access device.

IC card 710 includes wireless interface (I/F) circuit 720, antenna 730, and gas detection device 740.

With the use of antenna 730, wireless I/F circuit 720 receives wireless power from reader/writer 750 and also performs wireless communication with reader/writer 750.

Gas detection device 740 is configured using any one of gas detection devices 1010, 1020, and 1030 described in Embodiment 1. Gas detection device 740 performs each operation of hydrogen-containing gas detection, reset, or refreshing, using the power received by wireless I/F circuit 730, and notifies reader/writer 750 of the result of the operation via wireless I/F circuit 720. The operation result to be notified may include a result of the hydrogen-containing gas detection.

Wireless I/F circuit 720, antenna 730, and gas detection device 740 are provided, for example, inside an opening of a resin substrate, and gas detection device 740 may contact, via the opening, fresh air in the surrounding environment of the resin substrate.

Reader/writer 750 provides IC card 710 with power for operating gas detection device 740 as well as wirelessly receives the result of the operation of gas detection device 740 from IC card 710 and presents the received operation result to the user. A display, buzzer, or vibrator, for example, may be used for the presentation of the operation result.

According to the above-described configuration, a wirelessly-drivable gas detection device is realized in a general form exemplified by IC card 710, with a low cost and a reduced size. Since the power source of gas detection device 740 can be provided without any contacts with others, the device itself cannot be an ignition point and a complicated work for explosion proof is unnecessary. Accordingly, a gas sensor system that is simple and easy to install can be attained.

IC card 710 including gas detection device 740 is provided in a place one wants to monitor for gas leaks, for example, in a hydrogen plant, a hydrogen station, a gas pipe line, or in a fuel cell vehicle. A person who monitors carries reader/writer 750 on the body and holds reader/writer 750 over IC card 710 that is placed, to get informed of a gas leak and identify the location of the gas leak. Reader/writer 750 may be carried not only by a person who monitors but also on a drone or a self-operating robot that visits around the locations at each of which IC card 710 is placed.

Note that IC card 710 is one example, not a limitation, of a wirelessly-drivable gas detection device, and may be realized in other form where appropriate.

IC card 710 may be embedded in a power source such as a button cell, perform each operation of hydrogen-containing gas detection, reset, or refreshing at all times, and notify a master device, such as reader/writer 750 or a tablet terminal, of the result of the operation via wireless I/F circuit 720.

Embodiment 3

The fuel cell vehicle according to Embodiment 3 includes the gas sensor described in Embodiment 1, and detects hydrogen gas in a vehicle, using the gas sensor.

Figure 12:
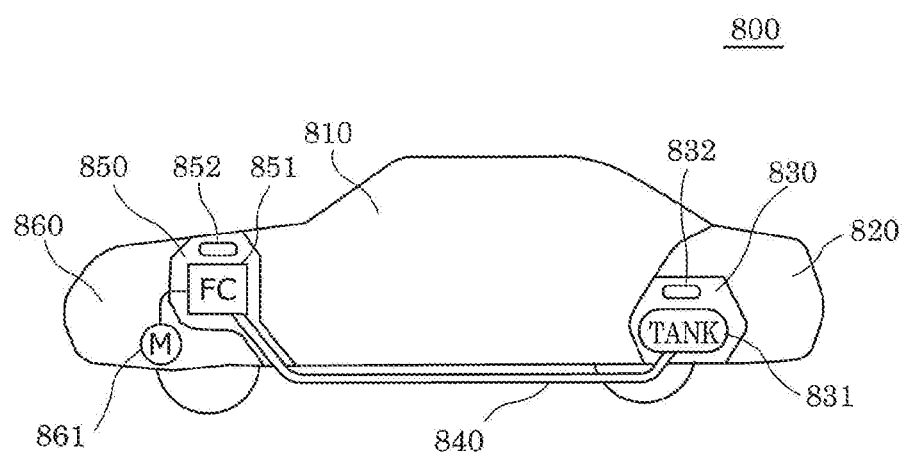
FIG. 12 is a pattern diagram illustrating an example of a configuration of a fuel cell vehicle according to Embodiment 3.

FIG. 12 is a pattern diagram illustrating an example of a configuration of a fuel cell vehicle according to Embodiment 3.

Fuel cell vehicle 800 includes passenger compartment 810, luggage compartment 820, gas tank compartment 830, fuel tank 831, pipe 840, fuel cell compartment 850, fuel cell 851, gas sensor 852, motor compartment 860, and motor 861.

Fuel tank 831 is placed in gas tank compartment 830 and preserves hydrogen gas as fuel gas. Gas sensor 832 detects a leak of fuel gas in gas tank compartment 830.

Fuel cell 851 includes a fuel cell stack composed of stacked cells each being a base unit including a fuel electrode, an air electrode, and an electrolyte. Fuel cell 851 is placed in fuel cell compartment 850. Hydrogen gas in fuel tank 831 is sent to fuel cell 851 in fuel cell compartment 850 through pipe 840. Fuel cell 851 generates electric power by allowing this hydrogen gas to react, in fuel cell 851, with oxygen gas in the atmosphere. Gas sensor 852 detects a leak of hydrogen gas in fuel cell compartment 850.

Motor 861 is placed in motor compartment 860. Motor 861 rotates by the electric power generated by fuel cell 851, and this causes fuel cell vehicle 800 to travel.

As described above, with the gas sensor according to the present disclosure, it is possible to detect hydrogen-containing gas using a very low power consumption of approximately 0.01 mV, for example. Accordingly, it is possible to monitor for hydrogen gas leaks at all times by utilizing the excellent power saving capability of the gas sensor, without significantly increasing the stand-by power of the fuel cell vehicle.

For example, a predetermined voltage may be applied at all times to gas sensors 832 and 852, regardless of the operation state of the ignition key of fuel cell vehicle 800. In such a case, whether hydrogen gas is present outside fuel tank 831 in gas tank compartment 830 and outside fuel cell 851 in fuel cell compartment 850 may be determined based on the amounts of the currents flowing through gas sensors 832 and 852.

Accordingly, whether a hydrogen gas leak is present has already been determined at the time when the operation of the ignition key is received, for example. The start-up time of the fuel cell vehicle can be shortened, compared to the case of driving the gas sensor for determining whether a hydrogen gas leak is present after the operation of the ignition key has been received. In addition, the safety of the fuel cell vehicle can be enhanced by continuously monitoring for hydrogen gas leaks after the fuel cell vehicle started traveling and even after the fuel cell vehicle has been housed in a garage, for example.

Supplementary Notes

As illustrated in FIG. 5, gas sensor 200 includes first electrode 103, resistive film 204 disposed on first electrode 103, and second electrode 106 disposed on resistive film 204. Resistive film 204 is one example of "metal-oxide layer" of the present disclosure. Resistive film 204 includes first metal-oxide layer 204a and second metal-oxide layer 204b. Resistive film 204 includes local region 105 and a bulk region surrounding local region 105. Here, "surrounding local region 105" does not exclusively means surrounding all of outer lateral surfaces of local region 105. In FIG. 5, a bulk region is a region other than local region 105 in second metal-oxide layer 204b. Local region 105 has a degree of oxygen deficiency higher than that of the bulk region. First metal-oxide layer 204a has a degree of oxygen deficiency higher than that of the bulk region. In FIG. 5, local region 105 is in contact with second electrode 106, penetrates through second metal-oxide layer 204b, and is not in contact with first electrode 103.

In FIG. 5, insulating film 107 has opening 107a. In opening 107a, part of the main surface of second electrode 106 is exposed from insulating film 107. The exposed surface of second electrode 106 is allowed to contact gas.

When gas containing hydrogen atoms is brought into contact with second electrode 106, a resistance value of local region 105 decreases, a resistance value of resistive film 204 decreases, and a resistance value of gas sensor 200 decreases.

Gas sensor 200 is included, for example, in gas detection device 1010 illustrated in FIG. 8A.

In power supply circuit 1012 in gas detection device 1010, a predetermined voltage is applied between first electrode 103 and second electrode 106 before the resistance value of resistive film 204 decreases, for example, and thereby, the resistance value of resistive film 204 increases. For example, the resistive state of resistive film 204 is set to a high-resistance state by a voltage applied, and subsequently transitions to a low-resistance state in response to hydrogen-containing gas. Alternatively, power supply circuit 1012 applies a predetermined voltage between first electrode 103 and second electrode 106 after the resistance value of resistive film 204 has decreased, for example, and thus increases the resistance value of resistive film 204. For example, the resistive state of resistive film 204 transitions to a low-resistance state in response to hydrogen-containing gas, and is subsequently set to a high-resistance state by a voltage applied. Alternatively, the resistive state of resistive film 204 may be set to a high-resistance state by a voltage applied, subsequently transition to a low-resistance state in response to hydrogen-containing gas, and after that, be reset again to the high-resistance state by a voltage applied.

Overview of Embodiments

The gas detection device according to one aspect includes: a gas sensor; and a drive circuit that applies a predetermined voltage to the gas sensor. The gas sensor includes: a first electrode; a second electrode; a metal-oxide layer that is disposed between the first electrode and the second electrode, and includes a bulk region and a local region surrounded by the bulk region, the local region having a degree of oxygen deficiency higher than a degree of oxygen deficiency of the bulk region; and an insulating film that covers the first electrode, the second electrode, and the metal-oxide layer, and has an opening that exposes part of a main surface of the second electrode. A resistance value of the metal-oxide layer decreases when the gas contacts the second electrode, the gas containing hydrogen atoms. When the resistance value of the metal-oxide layer falls outside a predetermined range that is set within a range of resistance values of the metal-oxide layer before the gas contacts the second electrode, the drive circuit applies the predetermined voltage between the first electrode and the second electrode to restore the resistance value back into the predetermined range.

With such a configuration, it is possible to stably operate the gas sensor over a long period of time since a characteristic fluctuation of the gas sensor is restored by the application of a predetermined voltage. As a result, a gas detection device having a simple structure and a long lifespan can be attained.

In addition, it is possible to attain excellent power saving and detection sensitivity by the following operation mechanism. That is, a current flowing between the first electrode and the second electrode concentrates in the local region having a high degree of oxygen deficiency. As a result, it is possible to increase the temperature of the local region with less current.

Since the local region generates heat by the current flowing between the first electrode and the second electrode, hydrogen atoms are dissociated from the hydrogen molecules, in a portion, of the second electrode, which contacts the local region, and a resistance value between the first electrode and the second electrode decreases by the dissociated hydrogen atoms bonding with oxygen atoms in the local region of a metal-oxide layer.

More specifically, the surface temperature of the second electrode rises as the temperature of the local region rises. The rise in these temperatures improves efficiency in the dissociation of the hydrogen atoms from the hydrogen molecules in the second electrode, which is set off by a catalytic action of the second electrode.

When hydrogen molecules that have passed the insulating film contact the second electrode, hydrogen atoms are dissociated from the hydrogen molecules and the dissociated hydrogen atoms diffuse in the second electrode to reach the local region. The dissociated hydrogen atoms then bond with oxygen in a metal oxide present in the local region to form water, and this decreases the resistance value between the first electrode and the second electrode.

Thus, by utilizing both self-heating and gas sensitivity in the local region formed inside the metal-oxide layer, it is possible to attain a gas sensor highly capable of saving power which is capable of detecting hydrogen-containing gas without heating with a heater.

The metal-oxide layer may have a layered structure in which a first metal-oxide layer including a first metal oxide and a second metal-oxide layer including a second metal oxide are stacked. The second metal-oxide layer may have a degree of oxygen deficiency lower than that of the first metal-oxide layer. The first metal-oxide layer may be in contact with the first electrode and the second metal-oxide layer may be in contact with the second electrode. The local region may be formed penetrating at least through the second metal-oxide layer to come into contact with the second electrode and may have a degree of oxygen deficiency higher than that of the second metal-oxide layer.

With such features, it is possible to attain a gas sensor that is highly capable of detecting hydrogen-containing gas since the layered structure having excellent resistance change characteristics is applied to the metal-oxide layer.

The second electrode may include a material having a catalytic action which causes hydrogen atoms to be dissociated from the molecules in the gas.

With such a feature, a resistance value between the first electrode and the second electrode decreases by the following: hydrogen atoms are dissociated from hydrogen molecules, at a portion, of the second electrode, which contacts the local region, and the dissociated hydrogen atoms bond with oxygen atoms in the local region of the metal-oxide layer.

The second electrode may include at least one selected from a group consisting of platinum, palladium, and iridium.

With such a feature, the second electrode is capable of causing hydrogen atoms to be dissociated from hydrogen molecules by a catalytic action of platinum or palladium.

The metal-oxide layer may have reversible resistance change characteristics of transitioning from a low-resistance state to a high-resistance state by a first voltage being applied, and transitioning from the high-resistance state to the low-resistance state by a second voltage being applied. The second voltage may have a polarity different from a polarity of the first voltage. The predetermined voltage may comprise the first voltage and the second voltage.

With such a feature, it is possible to more surely restore the characteristic fluctuation of the gas sensor by electrically rendering the resistive state of the metal-oxide layer firstly to be a low-resistance state and then changing it to a high-resistance state.

When the resistance value of the metal-oxide layer is below a lower limit of the predetermined range, the drive circuit may apply the predetermined voltage between the first electrode and the second electrode.

With such a feature, when a detection current deviates from a predetermined range and is below its lower limit, this is taken as an opportunity to restore the characteristic fluctuation of the gas sensor. Thus, it is possible to stably operate the gas sensor over a long period of time.

When the resistance value of the metal-oxide layer is above an upper limit of the predetermined range, the drive circuit may apply the predetermined voltage between the first electrode and the second electrode.

With such a feature, when a detection current deviates from a predetermined range and is above its upper limit, this is taken as an opportunity to restore the characteristic fluctuation of the gas sensor. Thus, it is possible to stably operate the gas sensor over a long period of time.

When the drive circuit applies the predetermined voltage between the first electrode and the second electrode and subsequently measures the resistance value of the metal-oxide layer, and the resistance value measured does not fall within the predetermined range, the drive circuit may apply again the predetermined voltage between the first electrode and the second electrode.

With such a feature, it is possible to more surely restore the characteristic fluctuation since a predetermined voltage is applied to the gas sensor the number of times required until the characteristic fluctuation of the gas sensor is restored.

When the drive circuit executes, up to a predetermined number of times, a process of applying the predetermined voltage between the first electrode and the second electrode a predetermined number of times and measuring the resistance value of the metal-oxide layer, and the resistance value measured still does not fall within the predetermined range, the drive circuit may determine that the restoration of the resistance value failed.

With such a feature, it is possible to detect a breakdown or a lifespan of the gas sensor through a failure in refreshing, and handle with it by exchanging devices, etc. at the right time.

The drive circuit may apply, to the gas sensor, a detection voltage whose absolute value is less than the predetermined voltage, to measure the resistance value of the metal-oxide layer.

With such a feature, it is possible to inhibit a change in the resistance value of the metal-oxide layer caused by an electrical factor since the resistance value of the metal-oxide layer is measured by the application of a low detection voltage.

The metal-oxide layer may include at least one of a transition metal oxide or an aluminum oxide.

With such a feature, it is possible to attain a gas sensor that is highly capable of detecting hydrogen-containing gas since the metal-oxide layer includes a transition metal oxide or an aluminum oxide having excellent resistance change characteristics.

The transition metal oxide may be a tantalum oxide, a hafnium oxide, or a zirconium oxide.

With such a feature, it is possible to attain a gas sensor that is highly capable of detecting hydrogen-containing gas since a tantalum oxide, a hafnium oxide, or a zirconium oxide having excellent resistance change characteristics is used for the transition metal oxide.

The resistance value of the metal-oxide layer may decrease by the following: the hydrogen atoms are dissociated from the molecules in the gas, at a portion, of the second electrode, which contacts the local region, and the hydrogen atoms dissociated bond with oxygen atoms in the local region of the metal-oxide layer, in a state in which heat is generated in the local region by the application of the detection voltage.

With such a feature, a current flowing between the first electrode and the second electrode concentrates in the local region having a high degree of oxygen deficiency. As a result, it is possible to increase the temperature of the local region with less current.

Since the local region generates heat by the current flowing between the first electrode and the second electrode, hydrogen atoms are dissociated from hydrogen molecules, at a portion, of the second electrode, which contacts the local region, and the dissociated hydrogen atoms bond with oxygen atoms in the local region of the metal-oxide layer. This decreases a resistance value between the first electrode and the second electrode.

More specifically, the surface temperature of the second electrode rises as the temperature of the local region rises. The rise in these temperatures, improves efficiency in the dissociation of the hydrogen atoms from the gas molecules containing the hydrogen atoms in the second electrode, which is set off by the catalytic action of the second electrode.

When the gas molecules which have passed the insulating film contact the second electrode, hydrogen atoms are dissociated from the gas molecules and the dissociated hydrogen atoms diffuse in the second electrode to reach a local region. The dissociated hydrogen atoms then bond with oxygen in a metal oxide present in the local region to form water, and this decreases a resistance value between the first electrode and the second electrode.

Thus, by utilizing both self-heating and gas sensitivity in the local region formed inside the metal-oxide layer, it possible to attain a gas sensor highly capable of saving power which is capable of detecting hydrogen-containing gas without heating with a heater.

The gas sensor according to one aspect of the present disclosure includes: the gas detection device; a wireless interface circuit that is connected to the gas detection device and wirelessly communicable with an external device; and an access device that obtains, through wireless communication, data related to the resistance value of the metal-oxide layer in the gas detection device via the wireless interface circuit.

With such a configuration, power saving capability, detection sensitivity, and a long lifespan of a gas detection device are exerted in the gas sensor system. A power for operating the gas detection device may be wirelessly transmitted from the access device or button cells may be mounted on the gas detection device. In such a case, since a power source can be provided without any contacts with others, the device itself cannot be an ignition point and a complicated work for explosion proof is unnecessary. Accordingly, it is possible to attain a gas sensor system that is simple and easy to install.

The fuel cell vehicle according to one aspect of the present disclosure includes: a passenger compartment; a gas tank compartment in which a hydrogen gas tank is placed;

a fuel cell compartment in which a fuel cell is placed; and the gas detection device, wherein the gas detection device is placed in at least one of the gas tank compartment or the fuel cell compartment.

With such a configuration, power saving capability, detection sensitivity, and a long lifespan of a gas detection device can be exerted in the fuel cell vehicle.

The hydrogen detection method according to one aspect of the present disclosure is a hydrogen detection method using a gas sensor. The gas sensor includes: a first electrode; a second electrode; a metal-oxide layer that is disposed between the first electrode and the second electrode, and includes a bulk region and a local region surrounded by the bulk region, the local region having a degree of oxygen deficiency higher than a degree of oxygen deficiency of the bulk region; and an insulating film that covers the first electrode, the second electrode, and the metal-oxide layer, and has an opening that exposes part of a main surface of the second electrode. The hydrogen detection method includes: detecting gas containing hydrogen atoms by detecting a decrease in a resistance value of the metal-oxide layer; determining whether the resistance value of the metal-oxide layer falls outside a predetermined range that is set within a range of resistance values of the metal-oxide layer before the gas contacts the second electrode, and when it is determined that the resistance value falls outside the predetermined range, applying a predetermined voltage between the first electrode and the second electrode to restore the resistance value of the metal-oxide layer back into the predetermined range.

With such a method, it is possible to stably operate the gas sensor over a long period of time since the characteristic fluctuation of the gas sensor is restored by the application of a predetermined voltage to the gas sensor. This, as a result, enables the gas sensor with a simple structure to have a longer lifespan. In addition, the gas sensor generates heat only with a current for detecting a resistive state of the gas sensor and detects hydrogen-containing gas without heating with a separate heater. Such a gas sensor enables hydrogen detection with excellent power saving.

INDUSTRIAL APPLICABILITY

A gas detection device according to the present disclosure is useful, for example, for use in fuel cell vehicles, hydrogen stations, hydrogen plants, etc.

The invention claimed is:

1. A gas detection device, comprising:
a gas sensor; and
a drive circuit that applies a predetermined voltage to the gas sensor, wherein
the gas sensor includes:
a first electrode;
a second electrode;
a metal-oxide layer that is disposed between the first electrode and the second electrode, and includes a bulk region and a local region surrounded by the bulk region, the local region having a degree of oxygen deficiency higher than a degree of oxygen deficiency of the bulk region; and
an insulating film that covers the first electrode, the second electrode, and the metal-oxide layer, and has an opening that exposes part of a main surface of the second electrode,
a resistance value of the metal-oxide layer decreases when the gas contacts the second electrode, the gas containing hydrogen atoms,
when the resistance value of the metal-oxide layer falls outside a predetermined range that is set within a range of resistance values of the metal-oxide layer before the gas contacts the second electrode, the drive circuit applies the predetermined voltage between the first electrode and the second electrode to restore the resistance value back into the predetermined range.

2. The gas detection device according to claim 1, wherein the metal-oxide layer comprises a first metal-oxide layer that is in contact with the first electrode and has a degree of oxygen deficiency higher than a degree of oxygen deficiency of the bulk region, and a second metal-oxide layer that is in contact with the second electrode and includes the bulk region, and
the local region is in contact with the second electrode and penetrates through the second metal-oxide layer.

3. The gas detection device according to claim 1, wherein the second electrode causes the hydrogen atoms to be dissociated from molecules contained in the gas.

4. The gas detection device according to claim 1, wherein the second electrode includes at least one selected from a group consisting of platinum, palladium, and iridium.

5. The gas detection device according to claim 1, wherein the metal-oxide layer has reversible resistance change characteristics of transitioning from a low-resistance state to a high-resistance state by a first voltage being applied, and transitioning from the high-resistance state to the low-resistance state by a second voltage being applied, the second voltage having a polarity different from a polarity of the first voltage, and
the predetermined voltage comprises the first voltage and the second voltage.

6. The gas detection device according to claim 1, wherein when the resistance value of the metal-oxide layer is below a lower limit of the predetermined range, the drive circuit applies the predetermined voltage between the first electrode and the second electrode.

7. The gas detection device according to claim 1, wherein when the resistance value of the metal-oxide layer is above an upper limit of the predetermined range, the drive circuit applies the predetermined voltage between the first electrode and the second electrode.

8. The gas detection device according to claim 1, wherein when the drive circuit applies the predetermined voltage between the first electrode and the second electrode and subsequently measures the resistance value of the metal-oxide layer, and the resistance value measured does not fall within the predetermined range, the drive circuit applies again the predetermined voltage between the first electrode and the second electrode.

9. The gas detection device according to claim 8, wherein when the drive circuit executes, up to a predetermined number of times, a process of applying the predetermined voltage between the first electrode and the second electrode a predetermined number of times and measuring the resistance value of the metal-oxide layer, and the resistance value measured still does not fall within the predetermined range, the drive circuit determines that the restoration of the resistance value failed.

10. The gas detection device according to claim 1, wherein
the drive circuit applies, to the gas sensor, a detection voltage whose absolute value is less than the predetermined voltage, to measure the resistance value of the metal-oxide layer.

11. The gas detection device according to claim 10, wherein the resistance value of the metal-oxide layer decreases by the following: the hydrogen atoms are dissociated from the molecules in the gas, at a portion, of the second electrode, which contacts the local region, and the hydrogen atoms dissociated bond with oxygen atoms in the local region of the metal-oxide layer, in a state in which heat is generated in the local region by the application of the detection voltage.

12. The gas detection device according to claim 1, wherein
the metal-oxide layer includes at least one of a transition metal oxide or an aluminum oxide.

13. The gas detection device according to claim 12, wherein
the transition metal oxide is a tantalum oxide, a hafnium oxide, or a zirconium oxide.

14. A gas sensor system, comprising:
the gas detection device according to claim 1;
a wireless interface circuit that is connected to the gas detection device and wirelessly communicable with an external device; and
an access device that obtains, through wireless communication, data related to the resistance value of the metal-oxide layer in the gas detection device via the wireless interface circuit.

15. A fuel cell vehicle, comprising:
a passenger compartment;
a gas tank compartment in which a hydrogen gas tank is placed;
a fuel cell compartment in which a fuel cell is placed; and
the gas detection device according to claim 1, wherein
the gas detection device is placed in at least one of the gas tank compartment or the fuel cell compartment.

16. A hydrogen detection method using a gas sensor,
the gas sensor including:
a first electrode;
a second electrode;
a metal-oxide layer that is disposed between the first electrode and the second electrode, and includes a bulk region and a local region surrounded by the bulk region, the local region having a degree of oxygen deficiency higher than a degree of oxygen deficiency of the bulk region; and
an insulating film that covers the first electrode, the second electrode, and the metal-oxide layer, and has an opening that exposes part of a main surface of the second electrode,
the hydrogen detection method comprising:
detecting gas containing hydrogen atoms by detecting a decrease in a resistance value of the metal-oxide layer;
determining whether the resistance value of the metal-oxide layer falls outside a predetermined range that is set within a range of resistance values of the metal-oxide layer before the gas contacts the second electrode, and
when it is determined that the resistance value falls outside the predetermined range, applying a predetermined voltage between the first electrode and the second electrode to restore the resistance value of the metal-oxide layer back into the predetermined range.

* * * * *